US010196676B2

(12) United States Patent
Bruinsma et al.

(10) Patent No.: US 10,196,676 B2
(45) Date of Patent: *Feb. 5, 2019

(54) ISOLATION OF NUCLEIC ACIDS

(71) Applicant: Exact Sciences Corporation, Madison, WI (US)

(72) Inventors: Janelle J. Bruinsma, Madison, WI (US); Michael J. Domanico, Middleton, WI (US); Graham P. Lidgard, Madison, WI (US); Hongzhi Zou, Middleton, WI (US); William G. Weisburg, San Diego, CA (US); Hemanth D. Shenoi, Verona, WI (US); James P. Light, II, Middleton, WI (US); Keith Kopitzke, Fallbrook, CA (US); John Zeis, San Marcos, CA (US)

(73) Assignee: Exact Sciences Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/046,669

(22) Filed: Jul. 26, 2018

(65) Prior Publication Data

US 2018/0327814 A1    Nov. 15, 2018

Related U.S. Application Data

(63) Continuation of application No. 15/807,970, filed on Nov. 9, 2017, now Pat. No. 10,047,390, which is a (Continued)

(51) Int. Cl.
*C12N 15/10* (2006.01)
*C12Q 1/6806* (2018.01)
(Continued)

(52) U.S. Cl.
CPC .......... *C12Q 1/6806* (2013.01); *B01D 33/15* (2013.01); *B01D 33/155* (2013.01); *B01L 3/00* (2013.01);
(Continued)

(58) Field of Classification Search
CPC ....................................................... C12Q 1/68
See application file for complete search history.

(56) References Cited

U.S. PATENT DOCUMENTS 4,458,066 A   7/1984   Caruthers et al.
4,683,058 A   7/1987   Lyman et al.
(Continued)

FOREIGN PATENT DOCUMENTS

CN   100368566   2/2008
CN   101307311   11/2008
(Continued)

OTHER PUBLICATIONS

Glockner et al. (Methylation of TFPI2 in stool DNA: a potential novel biomarker for the detection of colorectal cancer, Cancer Res. Jun. 1, 2009;69(11):4691-9. Epub May 12, 2009).*
(Continued)

*Primary Examiner* — Aaron A Priest
(74) *Attorney, Agent, or Firm* — Casimir Jones, S.C.; Mary Ann D. Brow

(57) ABSTRACT

Provided herein is technology relating to isolating nucleic acids. In particular, the technology relates to methods and kits for extracting nucleic acids from problematic samples such as stool.

8 Claims, 23 Drawing Sheets

Specification includes a Sequence Listing.

Related U.S. Application Data continuation of application No. 14/939,925, filed on Nov. 12, 2015, now Pat. No. 9,845,491, which is a continuation of application No. 14/713,289, filed on May 15, 2015, now Pat. No. 9,631,228, which is a continuation of application No. 14/145,082, filed on Dec. 31, 2013, now Pat. No. 9,163,278, which is a continuation of application No. PCT/US2012/037581, filed on May 11, 2012.

(60) Provisional application No. 61/485,338, filed on May 12, 2011, provisional application No. 61/485,448, filed on May 12, 2011, provisional application No. 61/485,386, filed on May 12, 2011, provisional application No. 61/485,214, filed on May 12, 2011.

(51) Int. Cl.
| | | |
|---|---|---|
| B03C 1/30 | (2006.01) | |
| B01D 33/15 | (2006.01) | |
| B01L 3/00 | (2006.01) | |
| B04B 3/00 | (2006.01) | |
| C12Q 1/6886 | (2018.01) | |

(52) U.S. Cl.
CPC .............. *B01L 3/5021* (2013.01); *B03C 1/30* (2013.01); *B04B 3/00* (2013.01); *C12N 15/1006* (2013.01); *C12N 15/1013* (2013.01); *C12N 15/1017* (2013.01); *C12Q 1/6886* (2013.01); *C12Q 2600/158* (2013.01); *C12Q 2600/16* (2013.01); *Y10T 436/143333* (2015.01)

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,965,188 | A | 10/1990 | Mullis et al. |
| 5,011,769 | A | 4/1991 | Duck et al. |
| 5,124,246 | A | 6/1992 | Urdea et al. |
| 5,288,609 | A | 2/1994 | Engelhardt et al. |
| 5,338,671 | A | 8/1994 | Scalice et al. |
| 5,403,711 | A | 4/1995 | Walder et al. |
| 5,409,818 | A | 4/1995 | Davey et al. |
| 5,494,810 | A | 2/1996 | Barany et al. |
| 5,508,169 | A | 4/1996 | Deugau et al. |
| 5,624,802 | A | 4/1997 | Urdea et al. |
| 5,639,611 | A | 6/1997 | Wallace et al. |
| 5,647,990 | A | 7/1997 | Vassarotti |
| 5,648,212 | A | 7/1997 | Albertsen et al. |
| 5,660,988 | A | 8/1997 | Duck et al. |
| 5,710,264 | A | 1/1998 | Urdea et al. |
| 5,773,258 | A | 6/1998 | Birch et al. |
| 5,792,614 | A | 8/1998 | Western et al. |
| 5,846,717 | A | 12/1998 | Brow et al. |
| 5,849,481 | A | 12/1998 | Urdea et al. |
| 5,851,770 | A | 12/1998 | Babon et al. |
| 5,882,867 | A | 3/1999 | Ullman et al. |
| 5,914,230 | A | 6/1999 | Liu et al. |
| 5,958,692 | A | 9/1999 | Cotton et al. |
| 5,965,408 | A | 10/1999 | Short |
| 5,985,557 | A | 11/1999 | Prudent et al. |
| 5,994,069 | A | 11/1999 | Hall et al. |
| 6,001,567 | A | 12/1999 | Brow et al. |
| 6,013,170 | A | 1/2000 | Meade |
| 6,063,573 | A | 5/2000 | Kayyem |
| 6,090,543 | A | 7/2000 | Prudent et al. |
| 6,110,677 | A | 8/2000 | Western et al. |
| 6,110,684 | A | 8/2000 | Kemper et al. |
| 6,121,001 | A | 9/2000 | Western et al. |
| 6,133,436 | A | 10/2000 | Koster et al. |
| 6,150,097 | A | 11/2000 | Tyagi et al. |
| 6,183,960 | B1 | 2/2001 | Lizardi |
| 6,210,884 | B1 | 4/2001 | Lizardi |
| 6,221,583 | B1 | 4/2001 | Kayyem et al. |
| 6,221,655 | B1 | 4/2001 | Fung et al. |
| 6,235,502 | B1 | 5/2001 | Weissman et al. |
| 6,248,229 | B1 | 6/2001 | Meade |
| 6,444,461 | B1 | 9/2002 | Knapp et al. |
| 6,872,816 | B1 | 3/2005 | Hall et al. |
| 6,992,182 | B1 | 1/2006 | Muller et al. |
| 7,005,266 | B2 | 2/2006 | Sprenger-Haussels |
| 7,387,874 | B2 | 6/2008 | Gocke et al. |
| 7,662,594 | B2 | 2/2010 | Kong et al. |
| 7,931,920 | B2 | 4/2011 | Hillebrand |
| 8,530,228 | B2 | 9/2013 | Han et al. |
| 8,574,890 | B2 | 11/2013 | Icenhour et al. |
| 8,808,990 | B2 | 8/2014 | Lidgard et al. |
| 8,980,107 | B2 | 3/2015 | Domanico et al. |
| 8,993,341 | B2 | 3/2015 | Bruinsma et al. |
| 8,999,176 | B2 | 4/2015 | Domanico et al. |
| 9,000,146 | B2 | 4/2015 | Bruinsma et al. |
| 9,057,098 | B2 | 6/2015 | Bruinsma et al. |
| 9,163,278 | B2 | 10/2015 | Bruinsma et al. |
| 9,169,511 | B2 | 10/2015 | Bruinsma et al. |
| 9,631,228 | B2 | 4/2017 | Bruinsma et al. |
| 9,845,491 | B2 | 12/2017 | Bruinsma et al. |
| 10,047,390 | B2 | 8/2018 | Bruinsma et al. |
| 2001/0035375 | A1 | 11/2001 | Humicke-Smith |
| 2002/0164631 | A1* | 11/2002 | Shuber ................ C12Q 1/6806 435/6.14 |
| 2003/0013112 | A1 | 1/2003 | Haussels |
| 2003/0173284 | A1 | 9/2003 | Baker |
| 2005/0026175 | A1 | 3/2005 | Link et al. |
| 2006/0172302 | A1 | 8/2006 | Hermansen et al. |
| 2006/0172331 | A1 | 8/2006 | Sprenger-Haussels |
| 2006/0270843 | A1 | 11/2006 | Hall et al. |
| 2007/0202525 | A1 | 8/2007 | Quake et al. |
| 2008/0299621 | A1 | 12/2008 | Tatnell et al. |
| 2009/0253142 | A1 | 10/2009 | Allawi et al. |
| 2010/0129828 | A1 | 5/2010 | Beaulieu et al. |
| 2010/0151456 | A1 | 6/2010 | Ataman-Onal et al. |
| 2011/0105346 | A1 | 5/2011 | Beattie et al. |
| 2012/0122088 | A1 | 5/2012 | Zou et al. |
| 2012/0122105 | A1 | 5/2012 | Oldham-Haltom et al. |
| 2012/0122106 | A1 | 5/2012 | Zou et al. |
| 2014/0193813 | A1 | 7/2014 | Bruinsma et al. |
| 2015/0010907 | A1 | 1/2015 | Lidgard et al. |
| 2015/0284770 | A1 | 10/2015 | Bruinsma et al. |
| 2016/0130635 | A1 | 5/2016 | Bruinsma et al. |
| 2018/0135105 | A1 | 5/2018 | Bruinsma et al. |

FOREIGN PATENT DOCUMENTS

| | | | |
|---|---|---|---|
| CN | 101680025 | 3/2010 | |
| CN | 101935647 | 7/2012 | |
| EP | 265244 | 4/1988 | |
| EP | 1371736 | 8/2006 | |
| JP | 2010-533851 | 10/2010 | |
| JP | 2010-533853 | 10/2010 | |
| WO | WO 1990011345 | 10/1990 | |
| WO | WO 2004108925 | 12/2004 | |
| WO | WO 2005023091 | 3/2005 | |
| WO | WO 2008084219 | 7/2008 | |
| WO | WO 2008150826 | 12/2008 | |
| WO | WO 2010014970 | 2/2010 | |
| WO | WO 2010028382 | 3/2010 | |
| WO | WO-2010028382 A2 * | 3/2010 | ......... A61B 10/0038 |
| WO | WO 2011014970 | 2/2011 | |
| WO | WO 2012002887 | 1/2012 | |
| WO | WO 2012155072 | 11/2012 | |

OTHER PUBLICATIONS

Fotedar et al. (Laboratory Diagnostic Techniques for *Entamoeba* Species, Clinical Microbiology Reviews, Jul. 2007, p. 511-532).*
Mangiapan et al. (Sequence capture—PCR improves detection of mycobacterial DNA in clinical specimens, J Clin Microbiol. May 1996;34(5):1209-15).*

(56) References Cited

OTHER PUBLICATIONS

Ahlquist et al., "HemoQuant, a new quantitative assay for fecal hemoglobin. Comparison with Hemoccoult," Ann Intern Med, 1984, 101:297-302.
Ahlquist et al., "Colorectal Cancer Screening by Detection of Altered Human DNA in Stool: Feasibility of a Multitarget Assay Panel," Gastroenterology, 2000, 119: 1219-1227.
Ahlquist et al., "Next Generation Stool DNA Testing for Detection of Colorectal Neoplasia—Early Marker Evaluation", poster presented at Colorectal Cancer: Biology to Therapy, American Association for Cancer Research Conference, Philadelphia, PA Oct. 27-30, 2010, 1 page.
Ahlquist et al., "Next-generation stool DNA test accurately detects colorectal cancer and large adenomas." Gastroenterology, 2012, 142:248-56.
Andreadis and Chrisey, "Use of immobilized PCR primers to generate covalently immobilized DNAs for in vitro transcription/translation reactions," Nucleic Acids Res, 2000, 28:e5, 8 pages.
Aquamira Technologies, "Some Important Words in Regards to Filter Ratings," retrived Oct. 3, 2014.
Ashland Inc., "PolyplasdoneTM crospovidone superdisintegrants," Product Overview, retrieved Jul. 26, 2016, 4 pages.
Ballabio, et al., "Screening for steroid sulfatase (STS) gene deletions by multiplex DNA amplification," Human Genetics, 1990, 84(6): 571-573.
Barnay, "Genetic disease detection and DNA amplification using cloned thermostable ligase," Proc. Natl. Acad. Sci USA, 1991, 88:189-93.
Beaucage et al., "Deoxynucleoside phosphoramidites—A new class of key intermediates for deoxypolynucleotide synthesis," Tetrahedron Lett., 1981, 22: 1859-1862.
Berthelet et al., "Rapid, direct extraction of DNA from soils for PCR analysis using polyvinylpolypyrrolidone spin columns," FEMS Microbiology Letters, 1996, 138:17-22.
Brown et al., "Chemical synthesis and cloning of a tyrosine tRNA gene," Meth Enzymol., 1979, 68:109-151.
Bustin, "Absolute quantification of mRNA using real-time reverse transcription polymerase chain reaction assays," J. Molecular Endocrinology, 2000, 25:169-193.
Chamberlain et al., "Deletion screening of the Duchenne muscular dystrophy locus via multiplex DNA amplification," Nucleic Acids Research, 1988, 16(23):11141-11156.
Cullen et al., "Simple and rapid method for direct extraction of microbial DNA from soil for PCR", Soil Biology and Biochemistry, vol. 30, No. 8/9, 1998, pp. 983-993.
Da Silva et al., "Fast and reliable extraction of protozoan parasite DNA from fecal specimens." Mol Diagn. Mar. 1999;4(1):57-64.
Don et al., "'Touchdown' PCR to circumvent spurious priming during gene amplification," Nucleic Acids Research, 1991, 19(14):4008.
Doulton USA, "Absolute Vs, Nominal Microns Pore Ratings," Retrieved Oct. 3, 2014, from http;//doultonusa.com/HTMLpages/absolute_vs_nominal_microns_rating.htm.
European Search Report dated Oct. 27, 2014, EP Patent Application No. 12782489.4, 9 pages.
Fotedar et al., "Labratory Diagnostic Techniques for *Entamoeba* Species," Clinical Microbiology Reviews, 2007, 20(3):511-532.
Glockner et al., "Methylation of TFPI2 in stool DNA: a potential novel biomarker for the detection of colorectal cancer," Cancer Res. Jun. 1, 2009;69(11):4691-9.
Guilfoyle et al., "Ligation-mediated PCR amplification of specific fragments from a class-II restriction endonuclease total digest," Nucleic Acids Research, 1997, 25:1854-1858.
Haaf et al., "Polymers of N-vinylpyrrolidone: synthesis, characterization, and uses," Polymer J., 1985, 17(1):143-152.
Hall et al., "Sensitive detection of DNA polymorphisms by the serial invasive signal amplification reaction," PNAS, 2000, 97:8272.
Hayden et al., "Multiplex-Ready PCR: A new method for multiplexed SSR and SNP genotyping," BMC Genomics, 2008, 9:80.

Hecker et al., "High and low annealing temperatures increase both specificity and yield in touchdown and stepdown PCR," Biotechniques, 1996, 20(3):478-485.
Herman et al., "Methylation-specific PCR: a novel PCR assay for methylation status of CpG islands," PNAS, 1996, 93(13):9821-9826.
Higuchi et al., "A general method of in vitro preparation and specific mutagenesis of DNA fragments: study of protein and DNA interactions," Nucleic Acids Research, 1988, 16(15):7351-7367.
Higuchi et al., "Kinetic PCR analysis: real-time monitoring of DNA amplification reactions," Biotechnology, 1993, 11:1026-1030.
Higuchi et al., "Simultaneous amplification and detection of specific DNA sequences," Biotechnology, 1992, 10:413-417.
Kalinina et al., "Nanoliter scale PCR with TaqMan detection," Nucleic Acids Research, 1997, 25:1999-2004.
Laboratory for Environmental Pathogents Research, Dept of Environmental Sciences, University of Toledo, "Polyvinylpyrrolidone (PVPP) cleanup of DNA samples," Dec. 2004, 2 pages.
Lenntech B.V., "Absolute rating vs. nominal rating for filters," www.lenntech.com/library/fine/absolute/absolute-nominal-filters.htm, retrieved Oct. 3, 2014, 1 page.
Lloyd-Jones et al., "Comparison of rapid DNA extraction methods applied to contrasting New Zealand soils." Soil Biology and Biochemistry, 2001, 33(15):2053-9.
Lyamichev et al., "Polymorphism identification and quantitative detection of genomic DNA by invasive cleavage of oligonucleotide probes," Nat. Biotech., 1999, 17:292-296.
Mangiapan et al. "Sequence Capture—PCR Improves Detection of Mycobacterial DNA in Clinical Specimens," Journal of Clinical Microbiology, 1996, 34. p. 1209-1215.
Matteucci et al., "Synthesis of deoxyoligonucleotides on a polymer support," J Am Chem Soc., 1981, 103:3185-3191.
Morgan et al., "Comparison of PCR and microscopy for detection of Cryptosporidium parvum in human fecal specimens: Clinical trial.," J. Clin. Microbiol., 1998, 36(4):995-98.
Narang et al., "Improved phosphotriester method for the synthesis of gene fragments," Meth Enzymol., 1979, 68: 90-98.
Nassuth et al., "Improved RNA extraction and one-tube RT-PCR assay for simultaneous detection of control plant RNA plus several viruses in plant extracts," J Virol Methods, 2000, 90:37-49.
Parham et al., "Specific Magnetic Bead-Based Capture of Genomic DNA from Clinical Samples: Application to the Detection of Group B Streptococci in Vaginal/Anal Swabs," Clinical Chemistry, 2007, 53:9, p. 1570-1576.
Person et al., "Towards a universally adaptable method for quantitative extraction of high-purity nucleic acids from soil." J Microbiolgical Methods, 2008, 75(1):19-24.
"PVP in Stool Samples," MadSci Network: Molecular Biology, Nov. 20, 2006.
Qiagen, QIAamp DNA Stool Mini Kit Handbook, Aug. 2001, 40 pages.
QIAamp® genomic DNA Kits, product information, Apr. 2008, 12 pages.
Rehmanji et al., "A novel stabilization of beer with Polyclar Brewbrite," MBAA TQ, 2002, 39(1):24-28.
Roux, "Using mismatched primer-template pairs in touchdown PCR," Biotechniques, 1994, 16(5):812-814.
Schouten et al., "Relative quantification of 40 nucleic acid sequences by multiplex ligation-dependent probe amplification," Nucleic Acids Research, 2002, 30(12): e57.
Shames et al., "Identification of widespread Heliobacter hepaticus infection in feces in commercial mouse colonies by culture and PCR assay," J. Clin. Mocrobiol, 1995, 33(11):2968-72.
Sigma-Aldrich Poly(vinylpolypyrrolidone) product information, retrieved Jun. 26, 2013, 2 pages.
St. John et al., "Rapid capture of DNA targets," BioTechniques, 2008, 44:259-264.
Stone et al., "Detection of rRNA from four respiratory pathogens using an automated Qbeta replicase assay," Mol Cell Probes, 1996, 10:359-370.
Stratagene, Gene Characterization Kits, product information, 1988, 2 pages.

(56) References Cited

OTHER PUBLICATIONS

Traverso et al., "Detection of Apc Mutations in Fecal DNA from Patients with Colorectal Tumors," N. Engl. J. Med., 2002, 346(5).
Triglia et al., "A procedure for in vitro amplification of DNA segments that lie outside the boundaries of known sequences," Nucleic Acids Res., 1988, 16:8186.
Trochimchuk et al., "A comparison of DNA extraction and purification methods to detect *Escherichia coli* O157:H7 in cattle manure," J Microbiol Methods, 2003, 54:165-175.
Verweij et al., "Detection and Identification of *Entamoeba* Species in Stool Samples by a Reverse Line Hybridization Assay," J Clin Microbiol., 2003, 41(11):5041-5045.
Vogelstein et al., "Digital PCR," PNAS, 1999, 96: 9236-41.
Weiner et al., "Kits and their unique role in molecular biology: a brief retrospective," Biotechniques, 2008, 44:701-704.
Whitney et al., "Enhanced Retrieval of DNA from Human Fecal Samples Results in Improved Performance of Colorectal Cancer Screening Test," JMD, 2004, 6(4).
Zhang et al., "An improved method for purifying genomic DNA from forest leaf litters and soil suitable for PCR", Journal of Soils and Sediments, 2009, vol. 9, No. 3, pp. 261-266.
Zou et al., Highly methylated genes in colorectal neoplasia: implications for screening. Cancer Epidemiol Biomarkers Prev. Dec. 2007;16(12):2686-96.
International Search Report and Written Opinion, dated Apr. 16, 2013, for International Patent PCT/US2012/037581, 21 pages.
European Search Report dated Aug. 11, 2017, for EP Patent Application No. 17170672.4, 10 pages.
Arnal et al., Comparison of seven RNA extraction methods on stool and shellfish samples prior to hepatitis A virus amplification. J Virol Methods. Jan. 1999;77(1):17-26.

\* cited by examiner

FIG. 1A

| |
|---|
| 1. Prepare clarified supernatant |
| Mix 8g stool with buffer |
| Centrifuge |
| Collect supernatant |
| Treat with inhibitor removal resin |
| Spin filter |
| Recover clarified supernatant |
| |
| 2. Sequential Capture of DNAs of Interest |
| Add Guanidine Isothiocyanate, heat |
| Add oligonucleotide-conjugated paramagnetic beads |
| (Alternatively, add the conjugated beads to the Guanidine Isothiocyanate solution, then heat) |
| Hybridize |
| |
| 3. Isolate Captured DNA |
| Pull beads from solution with magnet |
| Remove supernatant (re-use supernatant for capture of next target, Fig. 1B) |
| Wash Beads 3X |
| Elute DNA |

FIG. 8A
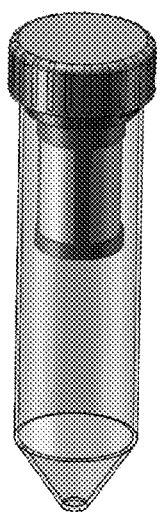
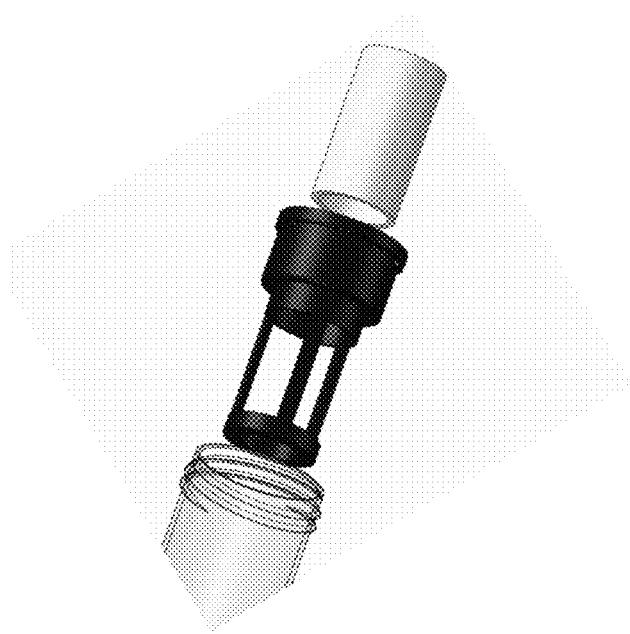
FIG. 8B

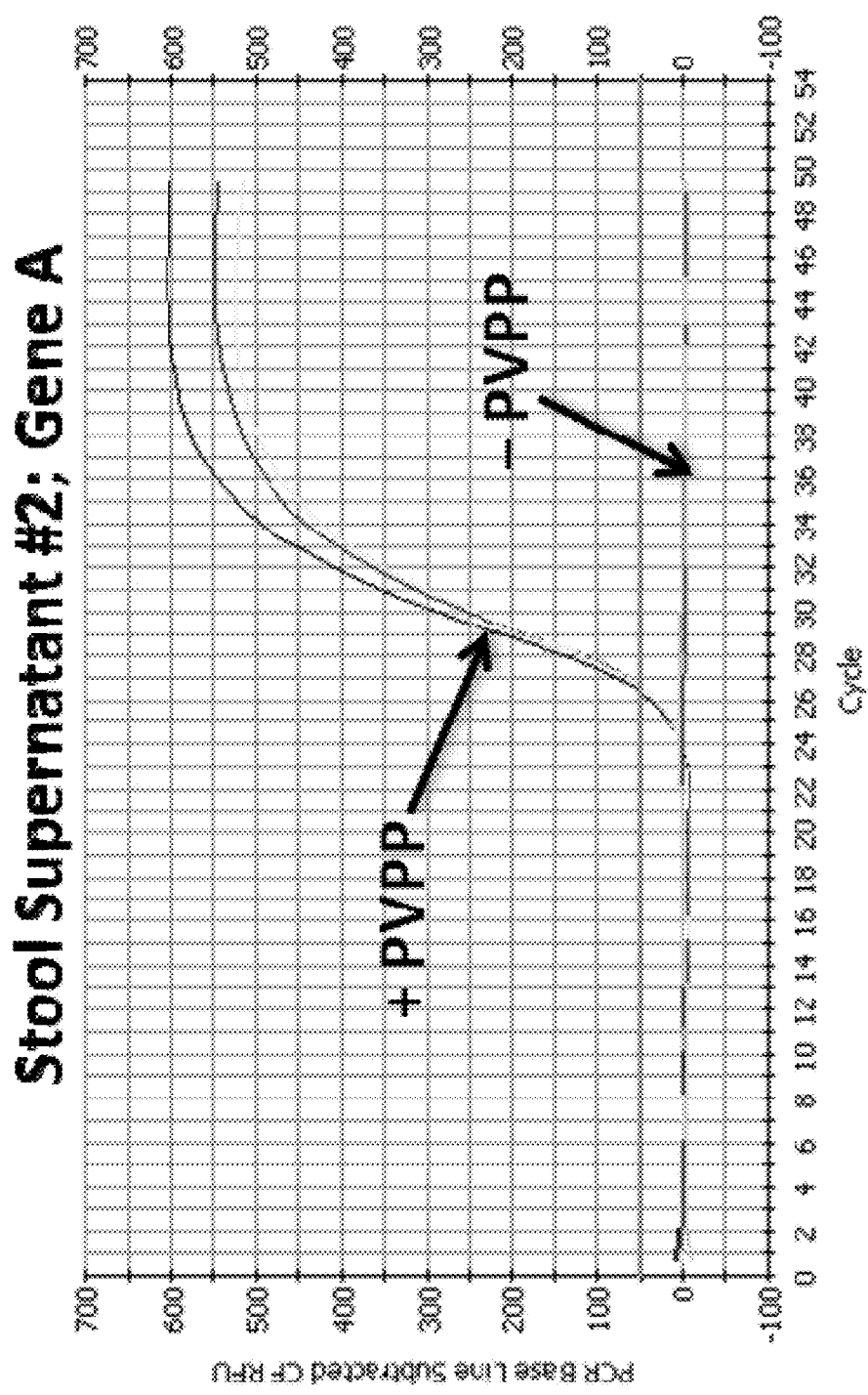

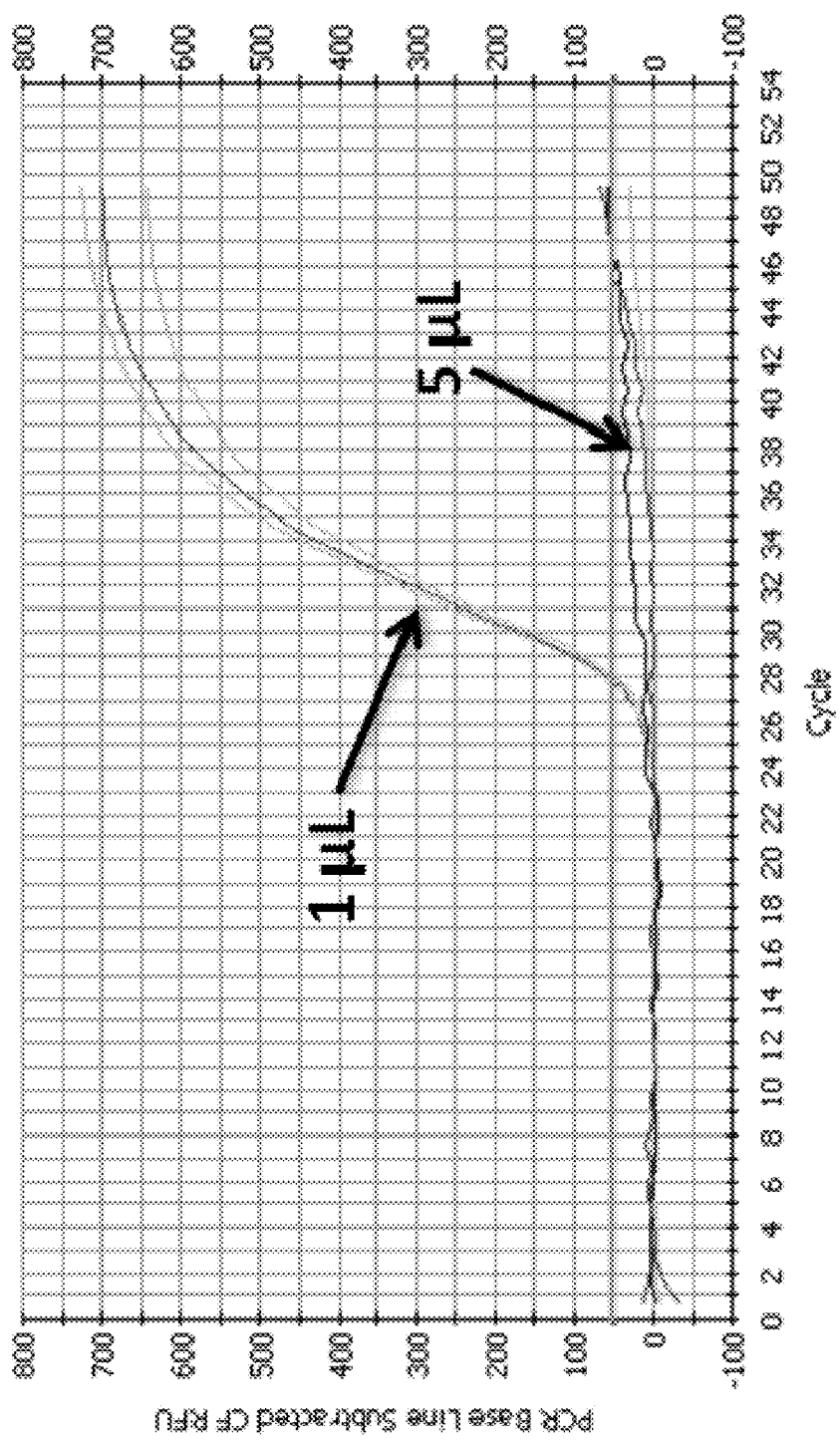

FIG. 11A
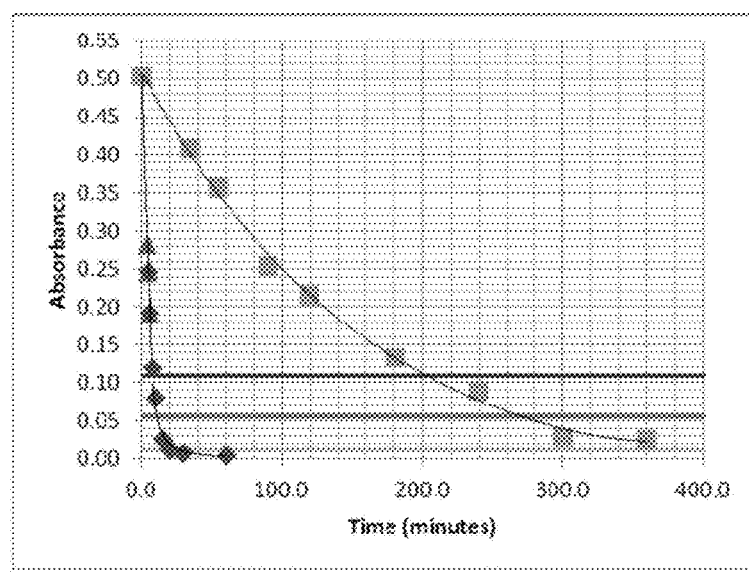
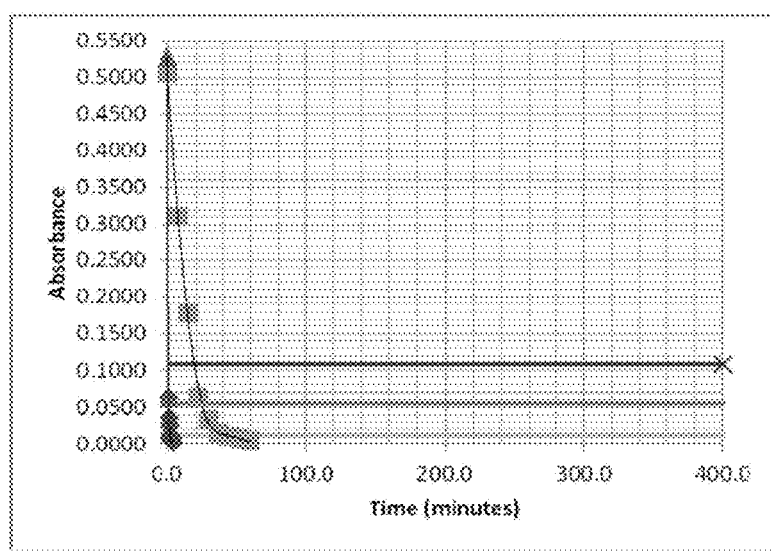
FIG. 11B

| Sample | Extraction | Strands/μL |
|---|---|---|
| Gene A | #1 | 2,020 |
|  | #2 | N/A |
| Gene V | #1 | 505 |
|  | #2 | N/A |

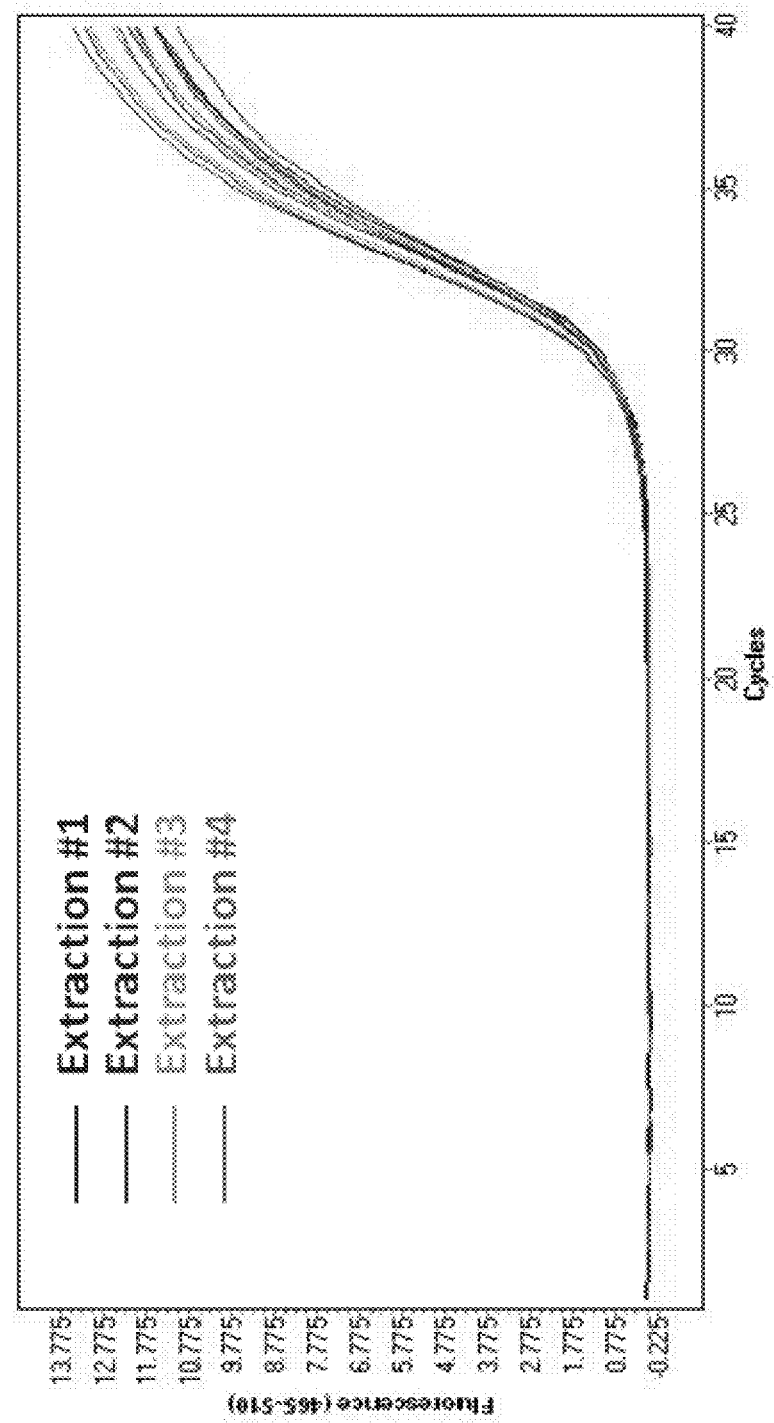

FIG. 14

| Process A | | Process B | |
|---|---|---|---|
| | Total Time(min) | | Total Time(min) |
| Prepare clarified supernatant | 55 | Prepare clarified supernatant | Overnight (e.g. 960 minutes) |
| Mix 8g stool with 32 ml buffer | | Mix 3 g stool with 7 vols buffer | |
| Centrifuge | | Centrifuge | |
| Collect supernatant (24 ml) | | Collect supernatant | |
| Treat 14 ml with inhibitor removal resin | | Filter through 0.45 μm filter | |
| Spin filter | | Recover clarified supernatant | |
| Recover clarified supernatant | | Precipitate with isopropanol to remove intrinsic streptavidin | |
| | | Centrifuge; discard supernatant | |
| | | Dissolve pellet in 4.9 ml TE buffer overnight | |
| Sequential Capture of DNAs of Interest | 15 | Parallel Capture of DNAs of Interest | 30 |
| Add Guanidine Isothiocyanate to 10 ml, heat | | To a 300 μL aliquot, add guanidine isothiocyanate and biotinylated probe oligonucleotide | |
| Add oligonucleotide-conjugated paramagnetic beads | | Hybridize | |
| Hybridize (60 minute per cycle) | 60 | Add streptavidin-coated paramagnetic beads | 15 |
| | | Hybridize oligonucleotide/DNA complexes to beads | |
| Isolate Captured DNA | 30 | Isolate Captured DNA | 15 |
| Pull beads from solution with magnet* | | Pull beads from solution with magnet | |
| Remove supernatant (reserve supe for next target capture) | | Remove and discard fluid | |
| Wash Beads | | Wash Beads | |
| Elute DNA | | Elute DNA | |
| Total Time of Purification (minutes) | 160 | Total Time of Purification (minutes) | 1020 |
| Equivalent Mass of Stool Yielding Purified Specific Gene DNA for Amplification | 2.0 gram | Equivalent Mass of Stool Yielding Purified Specific Gene DNA for Amplification | 0.18 gram |

*See text for improved magnet configuration

ISOLATION OF NUCLEIC ACIDS

The present application is a continuation of U.S. patent application Ser. No. 15/807,970, filed Nov. 9, 2017, now allowed, which is a continuation of U.S. patent application Ser. No. 14/939,925, filed Nov. 12, 2015, now U.S. Pat. No. 9,845,491, which is a continuation of U.S. patent application Ser. No. 14/713,289, filed May 15, 2015, now U.S. Pat. No. 9,631,228, which is a continuation of U.S. patent application Ser. No. 14/145,082, filed Dec. 31, 2013, now U.S. Pat. No. 9,163,278, which is a continuation of International Patent Application Serial Number PCT/US2012/03751, filed May 11, 2012, which claims the benefit of U.S. Provisional Patent Application Ser. Nos. 61/485,214, 61/485,338, 61/485,386, and 61/485,448, each of which was filed May 12, 2011, all of the above patent applications are incorporated herein by reference in their entirety.

FIELD OF INVENTION

Provided herein is technology relating to isolating nucleic acids. In particular, the technology relates to methods and kits for extracting nucleic acids from problematic samples such as stool.

BACKGROUND

Isolating specific target nucleic acids from a sample is an important step for many medical diagnostic assays. For example, certain mutations and methylation states in known genes are correlated, associated, and/or predictive of disease. DNA harboring these genes can be recovered from a sample and tested for the presence of the particular mutations and methylation states.

In practice, such assays require isolating and assaying several genetic targets from a sample. For many detection methods, detecting rare mutations or methylation events in a single gene requires isolating and testing a large quantity of DNA. This problem is compounded when assaying a panel of genes, each of which must be present in a large quantity for a robust diagnostic test. Thus, to detect rare mutations and methylation events in multiple genes, the isolated DNA must be highly concentrated and comprise a substantial portion of the detection assay.

This requirement imposes many problems, however. For example, preparing such quantities and concentrations of DNA requires a large sample as input (e.g., having a mass of several grams, e.g., approximately 2-4 grams) to provide sufficient nucleic acid for detection, and thus requires a method that can prepare DNA from a large sample. In addition, assay inhibitors are often isolated and concentrated with the DNA preparation. Consequently, concentrated DNA preparations produced by conventional methods also often retain unacceptable concentrations of inhibitors, which are then introduced into a subsequent assay. Moreover, if all targets of the panel are extracted simultaneously in a bulk, non-selective DNA preparation, the sensitivity of the assay is compromised because, as the preparation is divided into aliquots for testing, less extracted DNA from any one gene of the panel is present in the assay. If, on the other hand, all members of the panel are extracted and tested together and are thus present in the same assay mixture, the sensitivity of detecting any single particular target is compromised by the presence of the non-target DNA molecules.

In addition, if a particular diagnostic target is present in a complex sample, it will be present in a small amount relative to other materials—both nucleic acid and non-nucleic acid—in the sample, thus providing a challenge for analytical methods designed to detect it. For example, analyses of DNA from stool samples is complicated by the fact that bacteria compose approximately 60/o of the dry mass of feces and the remainder is largely the remains of plant and animal matter ingested as food by the subject. As such, the human subject's cells, which are only those that slough off the lining of the digestive tract, are a very small fraction of the stool and substantial amounts of nucleic acids from other sources are present. Furthermore, in assays to detect gene modifications indicative of colon cancer, cells derived from a tumor that may be present in the colon would compose only a small fraction of the human subject's gut cells that slough off the digestive tract lining. Consequently, cancer cells (and the DNAs they contain) make up a minimal amount of the stool mass. Such samples are also often very viscous, which presents problems in sample preparation and isolation of nucleic acid.

Conventional methods and kits for isolating DNA from samples typically prepare total DNA (e.g., by a non-specific precipitation method) from a sample. For complex samples such as stool samples, this is a particular drawback of conventional methods, as total DNA isolated from a stool sample comprises DNA from the gut-resident bacteria (and any viruses, eukaryotes, and archaea present) along with DNA from the subject. Moreover, conventional methods and kits are primarily designed to prepare DNA from small samples, e.g., samples having masses of less than 1 gram, e.g., 50 to 200 milligrams, limiting the yield of target nucleic acid from complex samples to very small amounts. Additional drawbacks are that most conventional technology does not effectively remove inhibitors and often require long processing steps, e.g., incubations. Consequently, conventional methods are not suited to high-sensitivity and high-specificity multi-gene panel analysis because they cannot prepare sufficient amounts of highly concentrated, inhibitor-free DNA from large samples, such as a stool sample of several grams. Assays using DNA prepared with conventional methods will not provide a sample that can be assayed with the required sensitivity threshold for detecting rare mutation or methylation events. Using a conventional method or kit to attain the starting quantities needed to attain such sensitivity requires multiple DNA extractions (e.g., the use of multiple kits) from multiple samples in addition to extra purification steps to remove inhibitors. Therefore, what is needed is a method of preparing concentrated, inhibitor-free DNA from a sample for each member of a gene panel for use in diagnostic assays.

SUMMARY

Provided herein is technology relating to isolating nucleic acids. In particular, the technology relates to methods, systems, and kits for extracting and purifying nucleic acids from exfoliated intestinal cells in stool specimens for use in quantitative and sensitive assays. The technology is embodied in a novel method for purifying specific DNA from stool that utilizes inhibitor removal steps and direct capture of DNA from stool supernatant, or a combination of these steps. The technology further provides filtration devices suitable for use with complex and viscous samples, such as stool samples. Accordingly, provided herein is a method for isolating a target nucleic acid from a sample, the method comprising removing an assay inhibitor, if present, from the sample to produce a clarified sample; capturing the target nucleic acid, if present, from the clarified sample with a capture reagent to form a capture complex; isolating the capture complex from the clarified sample; and recovering the target nucleic acid, if present, from the capture complex in a nucleic acid solution. In some embodiments the method further comprises retaining the clarified sample after the capturing step; and repeating the isolating and recovering steps using the retained clarified sample and a second capture reagent.

In some embodiments, removing the inhibitor comprises homogenizing the sample to produce a homogenate; centrifuging the homogenate to produce a supernatant; treating the supernatant with an inhibitor-adsorbing composition to bind the inhibitor, if present, in an inhibitor complex; and isolating the inhibitor complex from the supernatant to produce a clarified sample. The inhibitor-adsorbing composition in some embodiments is a polyvinylpyrrolidone. In some embodiments, the polyvinylpyrrolidone is insoluble and in some embodiments the polyvinylpyrrolidone is a polyvinylpolypyrrolidone. It is useful in some embodiments to provide the polyvinylpyrrolidone in a premeasured form, for example in some embodiments the polyvinylpyrrolidone is provided as a tablet. Various techniques are used to separate the inhibitor complex from the sample. For example, in some embodiments isolating the inhibitor complex comprises centrifuging to separate the inhibitor complex from the supernatant.

In some embodiments, the centrifuging comprises centrifuging through a spin column. Therefore, in some embodiments provided herein is technology relating to filtration and particularly, but not exclusively, to filters and methods for filtering by means of centrifugation. Specifically, some embodiments of the technology provided herein address the problem of spin filter clogging by providing technology in which both the bottom end and body of a spin filter are made from a porous or permeable material. That is, the walls of the spin filter are made of the same or similar material as that used for the filter means at the bottom end in conventional designs. As such, when the bottom portion of the filter becomes clogged during filtration, the walls provide additional surface through which the sample can be filtered.

This technology is provided herein as a spin filter comprising a hollow body, a bottom end, and an open top end opposite the bottom end, wherein the hollow body is made from a porous filtering material. In some embodiments the bottom end is made from a porous filtering material. The hollow body and bottom end of the spin filter assume any shape appropriate for the filtration application to which the filter is applied. For example, in some embodiments the hollow body is a tube and in some embodiments the bottom end is a hemisphere. In other embodiments, the bottom end is a disc, a cone, or a portion of an ellipsoid. Furthermore, the spin filter is made from any material that is appropriate for filtering a sample. Thus, in some embodiments the porous filtering material is polyethylene. Samples comprise varying sizes of particles, matter, precipitates, etc. that are to be removed by filtration. Accordingly, the filtering material can be selected to have physical properties that provide the desired separation. For example, in some embodiments the porous filtering material has a nominal pore size of 20 micrometers. In some embodiments, use of the filter produces a filtrate that a user retains for additional processing. As such, some embodiments provide a spin filter assembly comprising a spin filter as described and a collection vessel adapted to receive the spin filter and collect the filtrate.

Also provided herein are methods for producing a filtrate from a sample comprising placing a sample to be filtered into the spin filter and centrifuging the spin filter, wherein during centrifuging, a fraction of the sample passes through porous filtering material of said spin filter to produce a filtrate.

The technology can be provided as a kit for use in a sample separation. Embodiments of such a kit comprise a spin filter as described and an instruction for use. In some embodiments the kit further comprises a collection vessel. In some embodiments, a kit comprising a spin filter further comprises additional reagents and materials for sample preparation, e.g., for inhibitor removal and/or target nucleic acid isolation.

In some embodiments, the methods and systems of the technology comprise capturing a nucleic acid target. Capturing the target nucleic acid, in some embodiments, comprises exposing a sample, such as a clarified sample preparation, to a denaturing condition to produce a denatured sample; and binding target nucleic acid in the denatured sample to a capture reagent to form a capture complex. Many treatments and conditions find use in denaturing macromolecules such as DNA. For example, in some embodiments, the denaturing condition comprises heating, e.g., in some embodiments the denaturing condition comprises heating at 90° C. Supplementing the sample to be denatured facilitates the denaturing; accordingly, in some embodiments, the clarified sample further comprises a denaturant. In certain preferred embodiments, the denaturant comprises guanidine thiocyanate. Furthermore, in some embodiments the capture reagent comprises an oligonucleotide complementary to at least a portion of the target nucleic acid. In some preferred embodiments, the capture reagent comprises particle, e.g., a magnetic particle. The oligonucleotide, in some embodiments of the technology, hybridizes to at least a portion of the target nucleic acid, and thus in some embodiments, the binding step comprises hybridizing the oligonucleotide and the target nucleic acid. Isolating the capture reagent (e.g., the capture reagent/target nucleic acid complex) is accomplished in some embodiments by exposing the capture reagent to a magnetic field; that is, in some embodiments provided herein, the isolating step comprises exposing the capture complex to a magnetic field and in some embodiments exposing the capture complex to the magnetic field localizes the target nucleic acid. The magnetic field is produced by any appropriate magnet or magnetic device for the method. For example, in some embodiments the isolating step comprises placing the sample in a magnetic field produced by a first magnet oriented with its north pole in close proximity to the sample and a second magnet oriented with its south pole in close proximity to the sample; and waiting for a time sufficient to allow the magnetic field to move the magnetic particles to the desired location. A device for producing a strong magnetic field is described, for example, in U.S. patent application Ser. No. 13/089,116, incorporated by reference herein.

The technologies provide for recovering target nucleic acid from the capture reagent. In some embodiments, recovering the target nucleic acid comprises eluting the target nucleic acid from the capture complex, e.g., in some embodiments, by heating. In some embodiments, elution of the target nucleic acid from the capture complex comprises exposing the capture complex to high pH, e.g., in some embodiments, by adding a solution of sodium hydroxide.

In some embodiments, the technology provides methods, systems and kits for capturing multiple nucleic acids from a single sample, e.g., a stool sample. For example, provided herein are methods for isolating a nucleic acid from a stool sample comprising contacting a stool sample with a target-specific capture reagent; binding a target nucleic acid, when present, to the target-specific capture reagent to form a complex; isolating the complex comprising the target-specific capture reagent and the target nucleic acid, when present, from the stool sample; eluting the target nucleic acid, when present, from the complex to produce a target nucleic acid solution comprising the target nucleic acid, when present; and repeating the method using a different target-specific capture reagent. The methods are appropriate for large samples, e.g., having a mass of at least 4 grams. Moreover, each eluted target nucleic acid is sufficiently purified, sufficiently concentrated, and sufficiently free of inhibitors such that each eluted target nucleic acid, when present, is detected by a quantitative PCR when the target nucleic acid solution composes up to approximately one-third of a volume of the quantitative PCR.

In some embodiments of the methods provided, the target nucleic acid is a human target nucleic acid. In additional embodiments, the target nucleic acid is a DNA. While not limited in the means by which the nucleic acid is isolated from the stool sample, in some embodiments the target-specific capture reagent is a sequence-specific nucleic acid capture reagent. In some embodiments, the sequence-specific nucleic acid capture reagent is an oligonucleotide and in some embodiments the oligonucleotide is covalently attached to a magnetic or paramagnetic particle. Some embodiments provide that a magnet is used for the isolating step and some embodiments provide for the simultaneous isolation of more than one target using multiple target-specific capture reagents in a single isolation step.

The method is not limited in the types of samples that are processed. For example, in some embodiments the sample is a viscous sample, e.g., having a viscosity of more than ten centipoise in some embodiments and having a viscosity of more than twenty centipoise in some embodiments. Additionally, the samples are of a wide range of sizes. The methods are used to process samples having, in some embodiments, a mass of more than one gram and in some embodiments the sample has a mass of more than five grams.

The technology provided herein is directed to removing inhibitors from samples below an amount that inhibits an assay. Thus, in some embodiments, the method provides that the nucleic acid solution comprises a first amount of the assay inhibitor that is less than a second amount of the assay inhibitor, wherein the second amount of the assay inhibitor inhibits PCR when five microliters of the nucleic acid solution are used in a PCR having a volume of twenty-five microliters. In some embodiments, the nucleic acid solution comprises a first amount of the assay inhibitor that is less than a second amount of the assay inhibitor, wherein the second amount of the assay inhibitor inhibits PCR when one microliter of the nucleic acid solution is used in a PCR having a volume of twenty-five microliters.

The technology is related to medical molecular diagnostics wherein querying the state, presence, amount, sequence, etc., of a biological substance (e.g., a molecule) is used to aid a medical assessment. Accordingly, in some embodiments, the target nucleic acid is correlated with a disease state selected from the set consisting of colon cancer and adenoma.

The technology described herein is provided in a kit form in some embodiments—for example, embodiments provide that the technology is a kit for isolating a target nucleic acid from a sample comprising a capture reagent comprising an oligonucleotide covalently attached to a magnetic particle, an apparatus to produce a magnetic field, polyvinylpyrrolidone, and an instruction for use. In some embodiments, the kit further comprises a homogenization solution. In some embodiments, the kit further comprises an elution solution and in some embodiments the kit further comprises guanidine thiocyanate. In some embodiments, it is convenient for the polyvinylpyrrolidone to be in a premeasured form. For example, the polyvinylpyrrolidone is provided in a tablet or capsule in some embodiments. Some embodiments of the kit provide a spin filter for removing polyvinylpyrrolidone.

In some embodiments, the target nucleic acid is isolated using a magnetic field. As such, embodiments of the kits described herein provide an apparatus that produces a magnetic field. One device that is used to produce a magnetic field suitable for use with embodiments of the technology provided herein comprises two magnets or sets of magnets and places the north pole(s) of the first magnet or set of magnets in close proximity to the sample and the south pole(s) of the second magnet or set of magnets in close proximity to the sample. In some embodiments, the kits further provide a device for collecting a sample, e.g., a device having a body and a detachable sample capsule attached to the body, wherein the detachable sample capsule comprises a sample collection space adapted to enclose a sample (for example, as described in U.S. Pat. Appl. Ser. No. 61/476,707).

In some embodiments, the kit provides vessels (e.g., a tube, a vial, ajar, and the like) used to process samples and hold various compositions used to process samples or that result from processing samples. For example, in some embodiments the kit further comprises a vessel in which to hold the sample and in some embodiments the kit further comprises a vessel in which to hold the isolated target nucleic acid. The kit, in some embodiments, is used at a location other than where the sample is processed and/or where the analyte is assayed. Accordingly, in some embodiments the kit further comprises a shipping container.

The technology provided herein finds use in systems for preparing a nucleic acid from a sample. In some embodiments, the system comprises polyvinylpyrrolidone for removing an inhibitor from the sample, a reagent for capturing a target nucleic acid from the sample, and a functionality for producing a magnetic field. In some embodiments, the system further comprises a functionality for collecting the sample and in some embodiments the system further comprises a functionality for shipping the nucleic acid solution.

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIGS. 1A and 1B provide charts of aspects of the nucleic acid isolation process. FIG. 1A provides a chart showing the steps of the nucleic acid isolation process. FIG. 1B is a flowchart showing an embodiment of the process that finds use in the sequential extraction of multiple targets from the same sample as an aspect of the overall process of FIG. 1A.

FIG. 5A is a drawing of a disc-shaped, solid (e.g., non-porous or non-permeable) bottom end; FIG. 5B is a drawing of a disc-shaped, porous (permeable) bottom end; FIG. 5C is a drawing of a porous, conical bottom end.

FIGS. 8A and 8B are drawings of a spin filter comprising a body of a porous material and a bottom end provided by a filter support. FIG. 8A is an assembled view and FIG. 8B is an exploded view.

FIGS. 9A-D are plots showing the removal of inhibitors from a stool sample.

FIGS. 10A-D are plots showing that spin filtration improves the removal of inhibitors.

FIGS. 11A-B. FIG. 11A is a plot of data comparing the localization efficiency of the conventional technology for samples having viscosities of 1 centipoise and 25 centipoise. FIG. 11B is a plot of data comparing the localization efficiency of the magnetic localization device provided by Light and Miller (U.S. patent application Ser. No. 13/089,116) provided for samples having viscosities of 1 centipoise and 25 centipoise.

FIG. 12A is a plot showing the results of a quantitative PCR in which a single extraction from a stool sample recovers most of the target DNA. FIG. 12B shows the concentrations of Gene A and Gene V in nucleic acid solutions from a first extraction and a second extraction.

FIGS. 13A-D show plots showing the results of quantitative PCRs in which the recoveries of four target DNAs are similar regardless of the order in which the four target DNAs are extracted from a stool sample.

FIG. 14 provides a chart comparing the workflow of an embodiment (Process A) with an exemplary process for isolating DNA from stool samples using steps based on existing methods (Process B, see, e.g., WO 2010/028382).

DETAILED DESCRIPTION

Figure 1B:
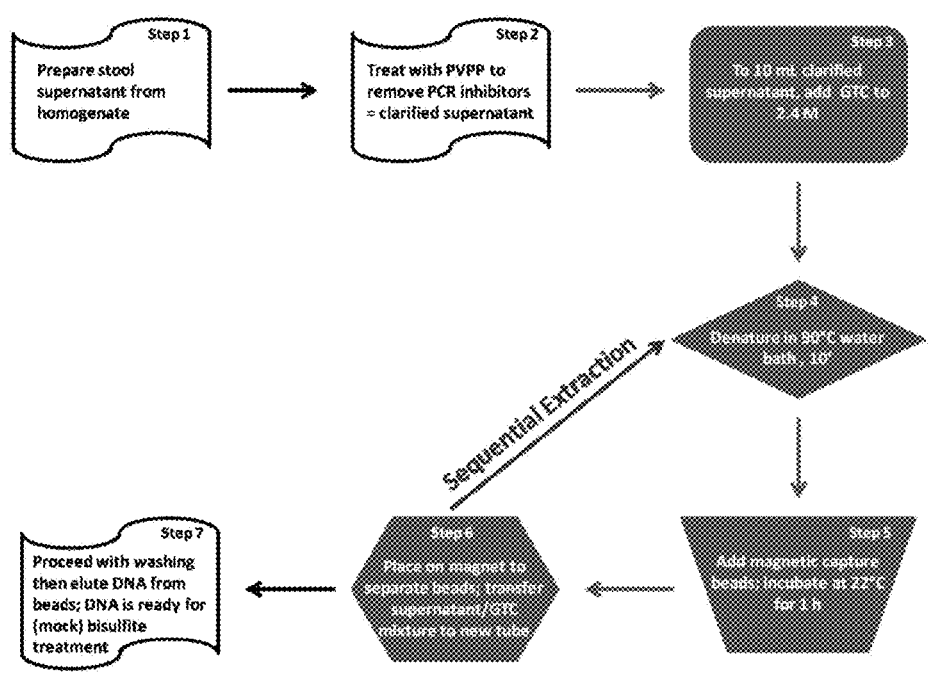

The present technology is related to producing DNA samples and, in particular, to methods for producing DNA samples that comprise highly purified, low-abundance nucleic acids in a small volume (e.g., less than 100, less than 60 microliters) and that are substantially and/or effectively free of substances that inhibit assays used to test the DNA samples (e.g., PCR, INVADER, QuARTS, etc.). Such DNA samples find use in diagnostic assays that qualitatively detect the presence of, or quantitatively measure the activity, expression, or amount of, a gene, a gene variant (e.g., an allele), or a gene modification (e.g., methylation) present in a sample taken from a patient. For example, some cancers are correlated with the presence of particular mutant alleles or particular methylation states, and thus detecting and/or quantifying such mutant alleles or methylation states has predictive value in the diagnosis and treatment of cancer.

Many valuable genetic markers are present in extremely low amounts in samples and many of the events that produce such markers are rare. Consequently, even sensitive detection methods such as PCR require a large amount of DNA to provide enough of a low-abundance target to meet or supersede the detection threshold of the assay. Moreover, the presence of even low amounts of inhibitory substances compromise the accuracy and precision of these assays directed to detecting such low amounts of a target. Accordingly, provided herein are methods providing the requisite management of volume and concentration to produce such DNA samples.

Some biological samples, such as stool samples, contain a wide variety of different compounds that are inhibitory to PCR. Thus, the DNA extraction procedures include methods to remove and/or inactivate PCR inhibitors. As such, provided herein is technology relating to processing and preparing samples and particularly, but not exclusively, to methods, systems, and kits for removing assay inhibitors from samples comprising nucleic acids.

Definitions

To facilitate an understanding of the present technology, a number of terms and phrases are defined below. Additional definitions are set forth throughout the detailed description.

As used herein, "a" or "an" or "the" can mean one or more than one. For example, "a" widget can mean one widget or a plurality of widgets.

As used herein, an "inhibitor" means any compound, substance, or composition, or combination thereof, that acts to decrease the activity, precision, or accuracy of an assay, either directly or indirectly, with respect to the activity, precision, or accuracy of the assay when the inhibitor is absent. An inhibitor can be a molecule, an atom, or a combination of molecules or atoms without limitation.

As used herein, the process of passing a mixture through a filter is called "filtration". The liquid produced after filtering a suspension of a solid in a liquid is called "filtrate", while the solid remaining in the filter is called "retentate", "residue", or "filtrand".

As used herein, "insoluble" refers to the property that a substance does not substantially dissolve in water and is essentially immiscible therewith. Upon separation of an aqueous phase from a non-aqueous phase, an insoluble substance does not partition into or partition with the aqueous phase.

As used herein, the terms "subject" and "patient" refer to any animal, such as a dog, cat, bird, livestock, and particularly a mammal, preferably a human. In some instances, the subject is also a "user" (and thus the user is also the subject or patient).

As used herein, the term "sample" and "specimen" are used interchangeably, and in the broadest senses. In one sense, sample is meant to include a specimen or culture obtained from any source, as well as biological and environmental samples. Biological samples may be obtained from animals (including humans) and encompass fluids, solids, tissues, and gases. Biological samples include blood products, such as plasma, serum, stool, urine, and the like. Environmental samples include environmental material such as surface matter, soil, mud, sludge, biofilms, water, crystals, and industrial samples. Such examples are not however to be construed as limiting the sample types applicable to the present invention.

The term "target," when used in reference to a nucleic acid capture, detection, or analysis method, generally refers to a nucleic acid having a feature, e.g., a particular sequence of nucleotides to be detected or analyzed, e.g., in a sample suspected of containing the target nucleic acid. In some embodiments, a target is a nucleic acid having a particular sequence for which it is desirable to determine a methylation status. When used in reference to the polymerase chain reaction, "target" generally refers to the region of nucleic acid bounded by the primers used for polymerase chain reaction. Thus, the "target" is sought to be sorted out from other nucleic acid sequences that may be present in a sample. A "segment" is defined as a region of nucleic acid within the target sequence. The term "sample template" refers to nucleic acid originating from a sample that is analyzed for the presence of a target.

As used herein, the term "locus" refers to a particular position, e.g., of a mutation, polymorphism, or a C residue in a CpG dinucleotide, within a defined region or segment of nucleic acid, such as a gene or any other characterized sequence on a chromosome or RNA molecule. A locus is not limited to any particular size or length, and may refer to a portion of a chromosome, a gene, functional genetic element, or a single nucleotide or basepair. As used herein in reference to CpG sites that may be methylated, a locus refers to the C residue in the CpG dinucleotide.

As used herein, a "collection liquid" is a liquid in which to place a sample to preserve, stabilize, and otherwise maintain its integrity as a representative sample of the specimen from which the sample was taken. While not limited in the types of compositions that find use as collection liquids, examples of collection liquids are aqueous buffers optionally comprising a preservative and organic solvents, such as acetonitrile.

As used herein, "a capture reagent" refers to any agent that is capable of binding to an analyte (e.g., a target). Preferably, "a capture reagent" refers to any agent that is capable of specifically binding to an analyte, e.g., having a higher binding affinity and/or specificity to the analyte than to any other moiety. Any moiety, such as a cell, a cellular organelle, an inorganic molecule, an organic molecule and a mixture or complex thereof can be used as a capture reagent if it has the requisite binding affinity and/or specificity to the analyte. The capture reagents can be peptides, proteins, e.g., antibodies or receptors, oligonucleotides, nucleic acids, vitamins, oligosaccharides, carbohydrates, lipids, small molecules, or a complex thereof. Capture reagents that comprise nucleic acids, e.g., oligonucleotides, may capture a nucleic acid target by sequence-specific hybridization (e.g., through the formation of conventional Watson-Crick basepairs), or through other binding interactions. When a capture oligonucleotide hybridizes to a target nucleic acid, hybridization may involve a portion of the oligonucleotide, or the complete oligonucleotide sequence, and the oligonucleotide may bind to a portion of or to the complete target nucleic acid sequence.

As used herein, "PVP" refers to polyvinylpyrrolidone, which is a water-soluble polymer made from the monomer N-vinylpyrrolidone. The term PVP is used herein to refer to PVP in various states of cross-linked polymerization, including preparations of PVP that may also be known in the art as polyvinylpolypyrrolidone (PVPP).

As used herein, a "magnet" is a material or object that produces a magnetic field. A magnet may be a permanent magnet or an electromagnet.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specfic PCR inverse PCR (see, e.g., Triglia, et al et al. (1988) Nucleic Acids Res., 16:8186; herein incorporated by reference in its entirety), ligation-mediated PCR (see, e.g., Guilfoyle, R. et al et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic or other DNA or RNA, without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons." Those of skill in the art will understand the term "PCR" encompasses many variants of the originally described method using, e.g., real time PCR, nested PCR, reverse transcription PCR (RT-PCR), single primer and arbitrarily primed PCR, etc.

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, (Hologic, Inc.) and are described, e.g., in U.S. Pat. Nos. 5,846,717, 5,985,557, 5,994,069, 6,001,567, 6,090,543, and 6,872,816; Lyamichev et al., Nat. Biotech., 17:292 (1999), Hall et al., PNAS, USA, 97:8272 (2000), and US 2009/0253142, each of which is herein incorporated by reference in its entirety for all purposes), enzyme mismatch cleavage methods (e.g., Variagenics, U.S. Pat. Nos. 6,110,684, 5,958,692, 5,851,770, herein incorporated by reference in their entireties); polymerase chain reaction (PCR), described above; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013.170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (e.g., Baranay Proc. Natl. Acad. Sci USA 88, 189-93 (1991)); and sandwich hybridization methods (e.g., U.S. Pat. No. 5,288,609, herein incorporated by reference in its entirety).

In some embodiments, target nucleic acid is amplified (e.g., by PCR) and amplified nucleic acid is detected simultaneously using an invasive cleavage assay. Assays configured for performing a detection assay (e.g., invasive cleavage assay) in combination with an amplification assay are described in US Patent Publication US 20090253142 A1 (application Ser. No. 12/404,240), incorporated herein by reference in its entirety for all purposes. Additional amplification plus invasive cleavage detection configurations, termed the QuARTS method, are described in U.S. patent application Ser. Nos. 12/946,737; 12/946,745; and Ser. No. 12/946,752, incorporated herein by reference in their entireties for all purposes.

The term "invasive cleavage structure" as used herein refers to a cleavage structure comprising i) a target nucleic acid, ii) an upstream nucleic acid (e.g., an INVADER oligonucleotide), and iii) a downstream nucleic acid (e.g., a probe), where the upstream and downstream nucleic acids anneal to contiguous regions of the target nucleic acid, and where an overlap forms between the a 3' portion of the upstream nucleic acid and duplex formed between the downstream nucleic acid and the target nucleic acid. An overlap occurs where one or more bases from the upstream and downstream nucleic acids occupy the same position with respect to a target nucleic acid base, whether or not the overlapping base(s) of the upstream nucleic acid are complementary with the target nucleic acid, and whether or not those bases are natural bases or non-natural bases. In some embodiments, the 3' portion of the upstream nucleic acid that overlaps with the downstream duplex is a non-base chemical moiety such as an aromatic ring structure, e.g., as disclosed, for example, in U.S. Pat. No. 6,090,543, incorporated herein by reference in its entirety. In some embodiments, one or more of the nucleic acids may be attached to each other, e.g., through a covalent linkage such as nucleic acid stem-loop, or through a non-nucleic acid chemical linkage (e.g., a multi-carbon chain).

As used herein, the terms "complementary" or "complementarity" used in reference to polynucleotides (i.e., a sequence of nucleotides) refers to polynucleotides related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "primer" refers to an oligonucleotide, whether occurring naturally, as in a purified restriction digest, or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like). The primer is typically single stranded for maximum efficiency in amplification, but may alternatively be partially or completely double stranded. The portion of the primer that hybridizes to a template nucleic acid is sufficiently long to prime the synthesis of extension products in the presence of the inducing agent. The exact lengths of the primers will depend on many factors, including temperature, source of primer and the use of the method. Primers may comprise labels, tags, capture moieties, etc.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth Enzymol. 68: 90-99; the phosphodiester method of Brown et al. (1979) Meth Enzymol. 68: 109-151; the diethylphosphoramidite method of Beaucage et al. (1981) Tetrahedron Lett. 22: 1859-1862; the triester method of Matteucci et al. (1981) J Am Chem Soc. 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

A "sequence" of a biopolymer refers to the order and identity of monomer units (e.g., nucleotides, amino acids, etc.) in the biopolymer. The sequence (e.g., base sequence) of a nucleic acid is typically read in the 5' to 3' direction.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," and "variant" refer to a gene or gene product that displays modifications in sequence and or functional properties (i.e., altered characteristics) when compared to the wild-type gene or gene product. It is noted that naturally occurring mutants can be isolated; these are identified by the fact that they have altered characteristics when compared to the wild-type gene or gene product.

As used herein, the term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment polypeptide are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (e.g., hnRNA); introns may contain regulatory elements (e.g., enhancers). Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

As used herein, the term "kit" refers to any delivery system for delivering materials. In the context of nucleic acid purification systems and reaction assays, such delivery systems include systems that allow for the storage, transport, or delivery of reagents and devices (e.g., inhibitor adsorbants, particles, denaturants, oligonucleotides, spin filters etc. in the appropriate containers) and/or supporting materials (e.g., buffers, written instructions for performing a procedure, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contains a subportion of the total kit components. The containers may be delivered to the intended recipient together or separately. For example, a first container may contain an materials for sample collection and a buffer, while a second container contains capture oligonucleotides and denaturant. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

The term "system" as used herein refers to a collection of articles for use for a particular purpose. In some embodiments, the articles comprise instructions for use, as information supplied on e.g., an article, on paper, or on recordable media (e.g., diskette, CD, flash drive, etc.). In some embodiments, instructions direct a user to an online location, e.g., a website.

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, percentage methylation, allele frequencies, RNA expression levels, protein expression, phenotypes correlating to genotypes, etc. "Allele frequency information" refers to facts or data pertaining to allele frequencies, including, but not limited to, allele identities, statistical correlations between the presence of an allele and a characteristic of a subject (e.g., a human subject), the presence or absence of an allele in an individual or population, the percentage likelihood of an allele being present in an individual having one or more particular characteristics, etc.

Embodiments of the Technology

Although the disclosure herein refers to certain illustrated embodiments, it is to be understood that these embodiments are presented by way of example and not by way of limitation.

1. Methods Generally

Provided herein are methods for isolating DNA, for example, from a stool sample. As summarized in FIG. 1, the process comprises homogenizing a sample (e.g., a stool sample) in a suitable buffer and preparing a supernatant from the homogenate. The supernatant is treated with a composition (e.g., a cross-linked polyvinylpyrrolidone (PVP) such as polyvinylpolypyrrolidone (PVPP)) to remove inhibitors and produce a clarified supernatant. DNA in the clarified supernatant is denatured, e.g., by adding guanidine thiocyanate (GTC) and/or by heating the sample. Then, a target capture reagent, e.g., a magnetic bead to which is linked an oligonucleotide complementary to the target, is added and the solution is incubated under conditions (e.g., ambient temperature for an hour) that promote the association (e.g., by hybridization) of the target with the capture reagent to produce a target:capture reagent complex. After isolating and removing the target:capture reagent complex (e.g., by application of a magnetic field), the resulting solution is heated again to denature the remaining DNA in the clarified supernatant and another target capture reagent can be added to isolate another target. The process can be repeated, e.g., at least four times, to isolate as many targets as are required for the assay (e.g., a sequential or serial extraction). The isolated target:capture reagent complexes from each capture and isolation step are washed and the target DNAs are eluted using a small volume of buffer suitable for downstream analysis.

2. Inhibitor Removal

The sample may be a sample of material that contains impurities that break down nucleic acids or inhibit enzymatic reactions. In particular, such impurities inhibit the catalytic activity of enzymes that interact with nucleic acids, e.g., nucleases such as restriction endonucleases, reverse transcriptases, nucleic acid polymerases, ligases, etc., particularly enzymes that are used for polymerase chain reaction (PCR), LCR (ligase chain reaction), TMA (transcription-mediated amplification), NASBA (nucleic acid base specific amplification), 3SR (self-sustained sequence replication), and the like.

2.1 PVP

Figure 2:
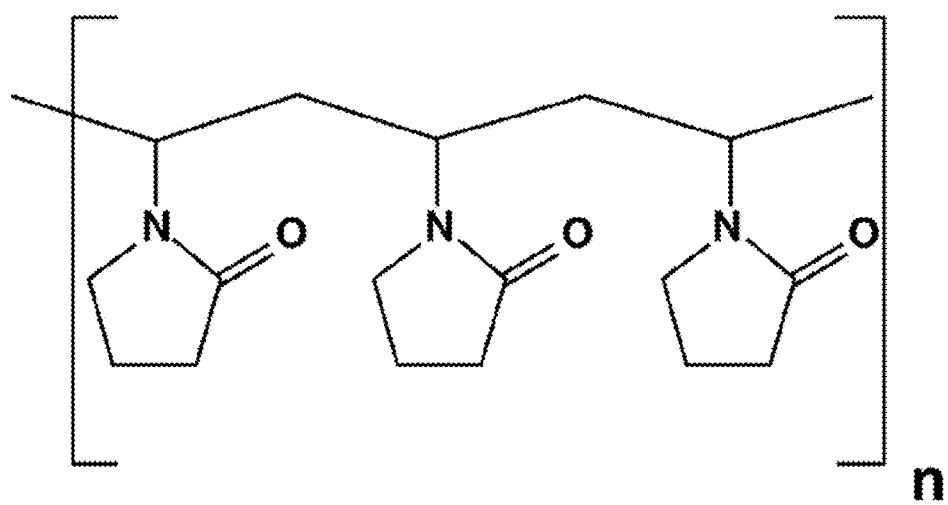
FIG. 2 is a chemical structure of a polyvinylpyrrolidone.
Figure 3:
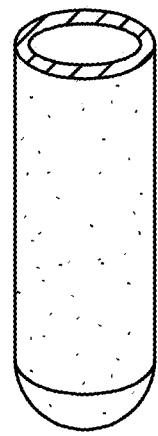
FIG. 3 is a drawing of an exemplary spin filter.
Figure 4:
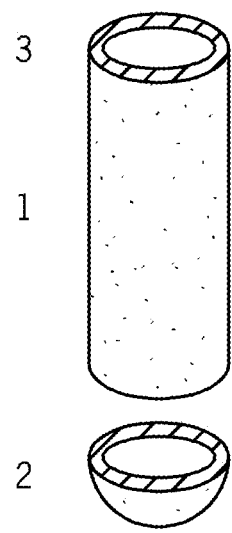
FIG. 4 is a drawing showing an exploded view of the spin filter shown in FIG. 3.
Figure 5A:
FIGS. 5A-5C are a series of drawings showing spin filter bottom ends associated with the spin filter of FIGS. 3 and 4.
Figure 5B:
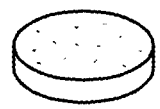
Figure 5C:
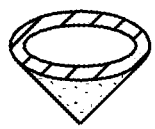
Figure 6:
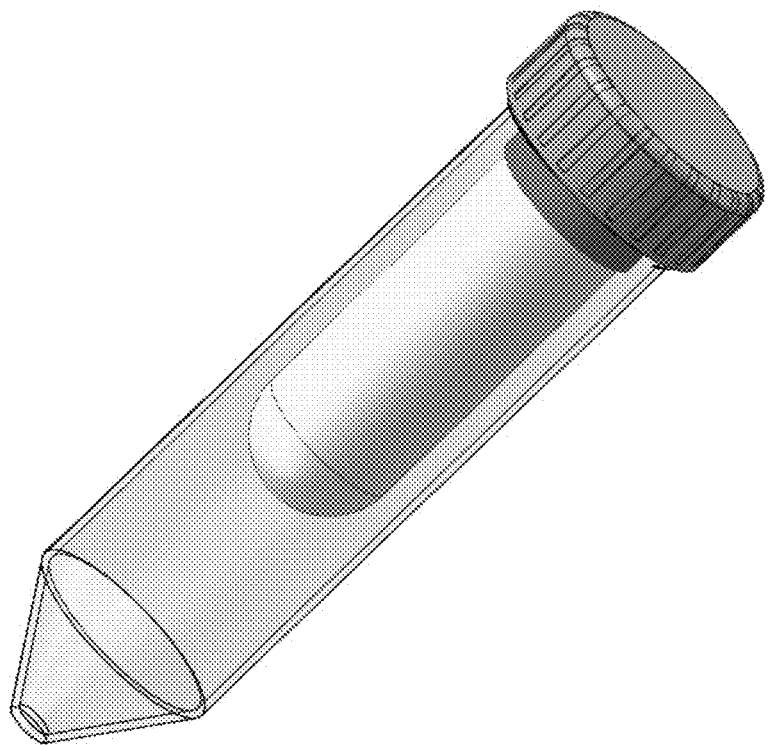
FIG. 6 is a drawing of a spin filter assembled with a collection tube.
Figure 7:
FIG. 7 is a cut-away drawing of the spin filter depicted in FIG. 6.

In some embodiments, inhibitors in a sample are removed by treatment with polyvinylpyrrolidone (see also, e.g., U.S. Pat. Appl. Ser. No. 61/485,338, which is incorporated herein by reference). Polyvinylpyrrolidone (PVP) is a water-soluble polymer made from the monomer N-vinylpyrrolidone (see FIG. 2). Polyvinylpolypyrrolidone (PVPP) is a highly cross-linked modification of PVP. The extent of cross-linking varies and there is no defined threshold establishing a division between PVP and PVPP. Accordingly, the term PVP is used herein to refer to PVP in various states of cross-linked polymerization, including preparations of PVP that may also be known in the art as PVPP. An important property, however, is that as the extent of cross-linking is increased, the polymer becomes increasingly insoluble in water. The cross-linked forms absorb water, which causes the polymer to swell. The synthesis and physical properties of PVP and PVPP are well-known in the art (e.g., see Haaf, Sanner, & Straub. *Polymers of N-vinylpyrrolidone: synthesis, characterization, and uses.* Polymer J. 17(1): 143 (1985)).

PVP has been used in many technical applications including use as a blood plasma expander; as a binder in many pharmaceutical tablets; as an adhesive in glue stick and hot melts; as an additive for batteries, ceramics, fiberglass, inks, inkjet paper and in the chemical-mechanical planarization process; as an emulsifier and disintegrant for solution polymerization; as photoresist; for production of membranes, such as dialysis and water purification filters; as a thickening agent in tooth whitening gels, etc.

PVP has also found use in binding impurities and removing them from solutions, particularly in wine-making and beer-making to remove polyphenols (see, e.g., Redmanji, Gopal, & Mola. *A novel stabilization of beer with Polyclar Brewbrite.* MBAA TQ 39(1): 24 (2002)). The use of soluble and insoluble forms of PVP has been described in relation to processing biological samples, for example, as a means to neutralize phenols (see, e.g., U.S. Pat. No. 7,005,266; Shames, et al. *Identification of widespread Helicobacter hepaticus infection in feces in commercial mouse colonies by culture and PCR assay.* J. Clin. Microbiol. 33(11): 2968 (1995); Morgan et al. *Comparison of PCR and microscopy for detection of Cryptosporidium parvum in human fecal specimens: Clinical trial.* J. Clin. Microbiol. 36(4): 995 (1998)).

The PVP is provided in forms that allow its introduction into a sample that is to be processed, e.g., as a powder, slurry, suspension, in granules, and the like. In some embodiments of the technology provided herein, the PVP is provided premeasured in a ready-to-use form. For example, in some embodiments, the PVP is pressed into a tablet comprising the mass of PVP appropriate for treating a sample. Different sizes and shapes of tablets are provided for different volumes and types of samples. Inert binders, fillers, and other compositions may be added to the tablets to provide physical, thermal, chemical, and biological stability, or to provide other desired characteristics such as improved dispersion within the sample or controlled-release.

Both the degree of cross-linking and the size of the PVP particles are parameters affecting the downstream assay of the resulting nucleic acid preparations. For example, soluble PVP has been found to inhibit some downstream assays. Accordingly, the method benefits from using a PVP that is sufficiently insoluble (e.g., sufficiently cross-linked) to allow adequate removal of the PVP by downstream processing steps (e.g., centrifugation and/or spin filtration). In addition, when the cross-linked PVP particles are too small they pack too tightly in the spin column and restrict the effluent flow of the sample into the spin column collection space. For example, experiments performed during the development of some embodiments of the present technology demonstrated that a PVP having an average particle size of 100-130 micrometers produced satisfactory results while a PVP having an average particle size of 30-50 micrometers restricted flow and filtration. Further experimentation may indicate that other sizes and solubilities may be appropriate for embodiments of the method.

2.2 Spin Filter

The technology provided herein encompasses use of a spin filter, for example, as provided in U.S. Pat. Appl. Ser. No. 61/485,214 to filter PVP-treated samples treated to remove inhibitors bound to the PVP. As discussed above, during the development of the PVP treatment method, experiments demonstrated that conventional spin columns having a filter frit in the bottom end clogged under some conditions. Accordingly, some embodiments of the technology comprise using a clog-resistant spin filter. FIGS. 3-8 depict various configurations of a clog-resistant spin filter in assembled and exploded views and associated with a collection tube. The clog-resistant filter is designed to allow the sample to be filtered through the body walls if the bottom end becomes clogged with residue from the sample.

Spin filters appropriate for use with the technology provided herein are generally made from a material is inert with respect to the sample—that is, the material does not react with or otherwise contaminate or modify the sample, other than filtering it, in a way that affects a subsequent assay (e.g., causes degradation of the sample, causes its decomposition, or the like). An example of such a material is polyethylene. Other suitable materials are, e.g., nylon, cellulose-acetate, polytetrafluoroethylene (PTFE, also known as Teflon), polyvinylidene fluoride (PVDF), polyester, and polyethersulfone. Operating pressure, the chemical and physical characteristics of the composition to be filtered, the size of the entity to remove from the sample, and the mechanical properties of the material (e.g., capability to withstand centrifugation at the speed required for the filtering application) are factors that are considered when selecting an appropriate spin filter.

Filters are manufactured to have various pore sizes appropriate for different filtering applications. For example, a filter with pore size of 0.2 micrometers is typically acknowledged to remove most bacteria while smaller pore sizes are required to remove viruses and bacterial spores. For removing larger particulates, a larger pore size is adequate. For example, while one aspect of the technology provided herein uses a spin filter having a 20-micrometer pore size, other pore sizes that find use in filtration applications are 0.22, 0.45, 10, 20, 30, and 45 micrometers. Accordingly, larger and smaller pore sizes are contemplated, as well as pore sizes intermediate within the intervals delimited by these particular values. For some filtration applications the filter is characterized by the average molecular weight of the molecules that are retained by the filter. For example, a filter with a 5,000 Da molecular weight cutoff (MWCO) is designed to retain molecules and complexes having at least a molecular weight of approximately 5,000 Da. Filters can provide MWCOs of 10,000 Da; 30,000 Da; 50,000 Da; 100,000 Da, and other limits required for the filtration task. Operating pressure and the size of the entity to remove from the sample are factors to consider when choosing a pore size or cutoff value.

3. Nucleic Acid Capture

The target nucleic acids are captured using a sequence-specific target capture reagent, e.g., a magnetic bead to which is linked an oligonucleotide complementary to the target.

After adding the capture reagent, the solution is incubated under conditions that promote the association (e.g., by hybridization) of the target with the capture reagent to produce a target:capture reagent complex. After isolating and removing the target:capture reagent complex (e.g., by application of a magnetic field), the resulting solution is heated again to denature the remaining DNA in the clarified supernatant and another target capture reagent can be added to isolate another target (e.g., by hybridization and application of a magnetic field). The process can be repeated, e.g., at least four times, to isolate as many targets as are required for the assay (e.g., a sequential or serial isolation process as described, e.g., by U.S. Pat. Appl. Ser. No. 61/485,386, which is incorporated herein by reference). Also, more than one target can be isolated in a capture step by using a capture reagent comprising multiple capture sequences.

3.1 Capture Reagents

In one aspect, the methods provided herein relate to the use of capture reagents. Such reagents are molecules, moieties, substances, or compositions that preferentially (e.g., specifically and selectively) interact with a particular target sought to be isolated and purified. Any capture reagent having desired binding affinity and/or specificity to the analyte target is used in the present technology. For example, in some embodiments the capture reagent is a macromolecule such as a peptide, a protein (e.g., an antibody or receptor), an oligonucleotide, a nucleic acid, (e.g., nucleic acids capable of hybridizing with the target nucleic acids), a vitamin, an oligosaccharide, a carbohydrate, a lipid, or a small molecule, or a complex thereof. As illustrative and non-limiting examples, an avidin target capture reagent may be used to isolate and purify targets comprising a biotin moiety, an antibody may be used to isolate and purify targets comprising the appropriate antigen or epitope, and an oligonucleotide may be used to isolate and purify a complementary oligonucleotide (e.g., a poly-dT oligonucleotide may be used to isolate and purify targets comprising a poly-A tail).

Any nucleic acids, including single-, double-, and triple-stranded nucleic acids, that are capable of binding, or specifically binding, to the target are used as the capture reagent in the present device. Examples of such nucleic acids include DNA, such as A-, B- or Z-form DNA, and RNA such as mRNA, tRNA and rRNA, aptamers, peptide nucleic acids, and other modifications to the sugar, phosphate, or nucleoside base. Thus, there are many strategies for capturing a target and accordingly many types of capture reagents are known to those in the art. While not limited in the means by which a target nucleic acid can be captured, embodiments of the technology provided herein comprise using an oligonucleotide that is complementary to the target and that thus captures the target by specifically and selectively hybridizing to the target nucleic acid.

In addition, target capture reagents comprise a functionality to localize, concentrate, aggregate, etc. the capture reagent and thus provide a way to isolate and purify the target when captured (e.g., bound, hybridized, etc.) to the capture reagent, e.g., when a target:capture reagent complex is formed. For example, in some embodiments the portion of the target capture reagent that interacts with the target (e.g., the oligonucleotide) is linked to a solid support (e.g., a bead, surface, resin, column) that allows manipulation by the user on a macroscopic scale. Often, the solid support allows the use of a mechanical means to isolate and purify the target:capture reagent complex from a heterogeneous solution. For example, when linked to a bead, separation is achieved by removing the bead from the heterogeneous solution, e.g., by physical movement. In embodiments in which the bead is magnetic or paramagnetic, a magnetic field is used to achieve physical separation of the capture reagent (and thus the target) from the heterogeneous solution. Magnetic beads used to isolate targets are described in the art, e.g., as described in U.S. Pat. No. 5,648,124 and European Pat. Appl. No. 87309308, incorporated herein by reference in their entireties for all purposes.

In some embodiments, the component of the capture reagent that interacts with the target (e.g., an oligonucleotide) is attached covalently to the component of the capture reagent that provides for the localization, concentration, and/or aggregation (e.g., the magnetic bead) of the target:capture reagent complex. Exemplary embodiments of such covalently-linked capture reagents are provided by Stone, et al. ("Detection of rRNA from four respiratory pathogens using an automated Qß replicase assay", *Molecular and Cellular Probes* 10: 359-370 (1996)), which is incorporated herein by reference in its entirety for all purposes. These covalently-linked capture reagents find use in the sequential isolation of multiple specific targets from the same sample preparation. Moreover, these capture reagents provide for the isolation of DNA targets without many of the problems that are associated with other methods. For example, the use of a conventional streptavidin bead to capture a biotinylated target is problematic for processing samples that comprise large amounts of free biotin (e.g., a stool sample) because the free biotin interferes with isolation of the target.

3.2 Magnetic Particle Localizer

The target:capture reagent complexes are captured using a magnetic particle localizer. However, sample viscosity can have a profound effect on localization efficiency due to the viscous drag affecting the magnetic microparticles. Stool samples have viscosities ranging from 20 centipoise to 40 centipoise, whereas, for reference, water at 20° C. has a viscosity of approximately 1 centipoise and honey at 20° C. has a viscosity of approximately 3,000 centipoise. Thus, for some applications, stronger magnetic fields may be preferred in order to provide for a more efficient isolation.

It has been found that particularly efficient isolations are obtained using magnetic devices having particular arrangements of magnets. For example, one particularly effective arrangement provides two sets of magnets circularly arranged in parallel planar layers around the sample, with the magnets in one layer oriented all with their north poles toward the sample and the magnets in the other layer are all oriented with their south poles toward the sample (i.e., the "N-S" configuration, as opposed to other orientations such as the "N-N" orientation in which all north poles or all south poles in both layers are oriented toward the sample). An example of such a device is provided by Light and Miller, U.S. patent application Ser. No. 13/089,116 ("Magnetic Microparticle Localization Device"), which is incorporated herein in its entirety for all purposes. In some configurations, the magnets of the device are arranged around a hole into which a sample tube (e.g., a 50 milliliter conical tube) is placed, such that they produce a magnetic flux in the sample. The magnetic flux effects the movement of the magnetic particles in the solution such that they are aggregated, concentrated, and/or isolated in an area of the sample tube that facilitates removal of the recovery of the target DNA (Light, supra).

Such devices have shown to be particularly effective for the localization of magnetic particles in large, viscous samples (e.g., stool samples) and thus are useful for the isolation of DNA from such samples (Light, supra). For example, FIGS. 11A and 11B show the effect of sample viscosity on the clearance of magnetic beads from solutions of 1 or 25 centipoise viscosity using conventional magnetic technology (11A) or the magnetic localization technology of Light and Miller (11B) (Light, supra). In the graphs shown, a decrease in absorbance indicates a decreased concentration of microparticles suspended in solution. The data collected for the 25 centipoise solutions are shown with squares (■) and data collected for the 1 centipoise solution are shown with diamonds (♦). These graphs show that the increase in viscosity slows the separation dramatically when conventional technology is used, while the Light and Miller magnetic particle localization device clears the more viscous solution with only a modest reduction in speed.

The chemistries and processes described above, when used in combination, provide a system for the isolation of nucleic acids from complex and inhibitory samples, such as stool samples, that is significantly faster than previously used methods. Moreover, the system produces nucleic acid preparations that are substantially more free of inhibitory substances and results in a higher yield of target nucleic acid for, e.g., diagnostic testing. Further, embodiments of this system are readily integrated into the laboratory workflow for efficient sample processing for use with any downstream analysis or detection technology. A comparison of the workflow, timeline, and process yields of an embodiment of the instant system and an exemplary conventional system is shown in FIG. 14.

4. Kits

It is contemplated that embodiments of the technology are provided in the form of a kit. The kits comprise embodiments of the compositions, devices, apparatuses, etc. described herein, and instructions for use of the kit. Such instructions describe appropriate methods for preparing an analyte from a sample, e.g., for collecting a sample and preparing a nucleic acid from the sample. Individual components of the kit are packaged in appropriate containers and packaging (e.g., vials, boxes, blister packs, ampules, jars, bottles, tubes, and the like) and the components are packaged together in an appropriate container (e.g., a box or boxes) for convenient storage, shipping, and/or use by the user of the kit. It is understood that liquid components (e.g., a buffer) may be provided in a lyophilized form to be reconstituted by the user. Kits may include a control or reference for assessing, validating, and/or assuring the performance of the kit. For example, a kit for assaying the amount of a nucleic acid present in a sample may include a control comprising a known concentration of the same or another nucleic acid for comparison and, in some embodiments, a detection reagent (e.g., a primer) specific for the control nucleic acid. The kits are appropriate for use in a clinical setting and, in some embodiments, for use in a user's home. The components of a kit, in some embodiments, provide the functionalities of a system for preparing a nucleic acid solution from a sample. In some embodiments, certain components of the system are provided by the user.

EXAMPLES

Example 1

Figure 9A:
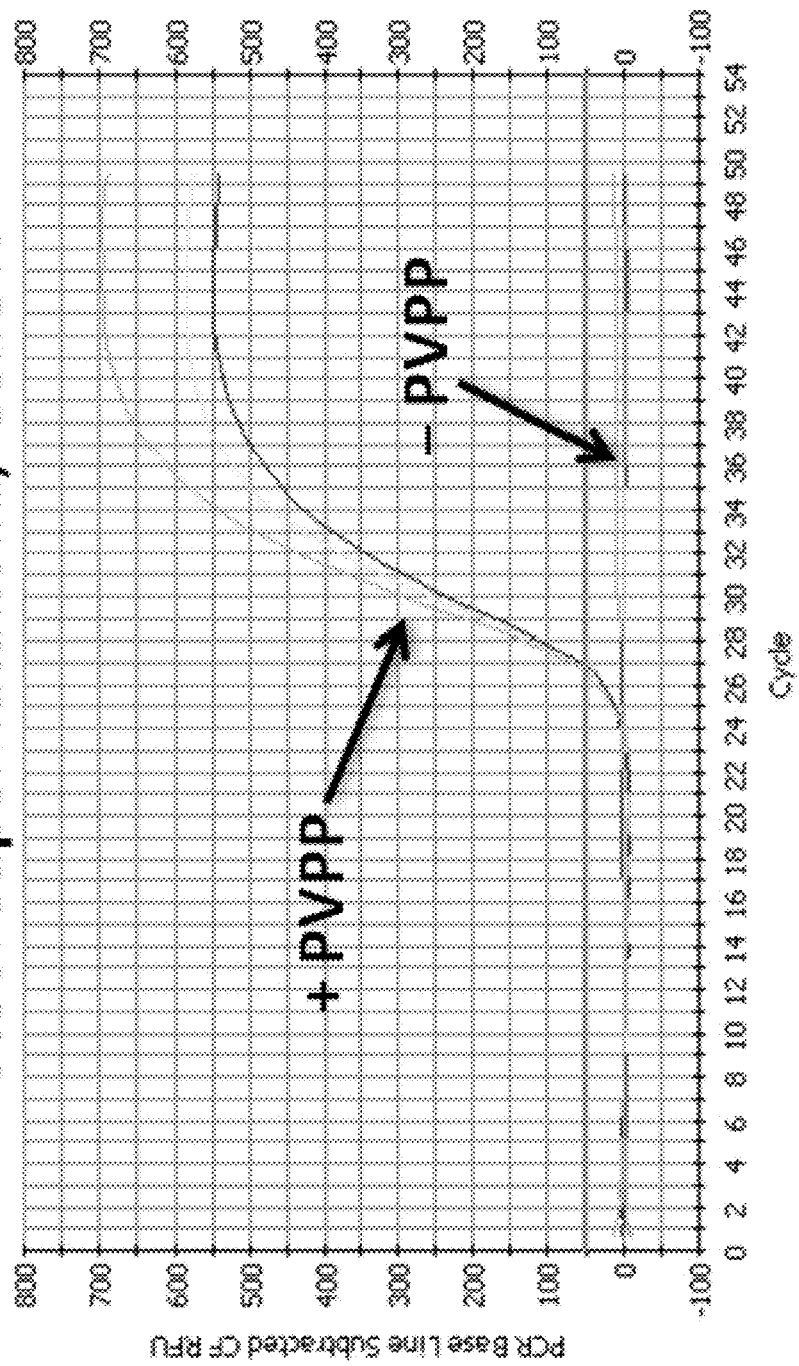
Figure 9B:
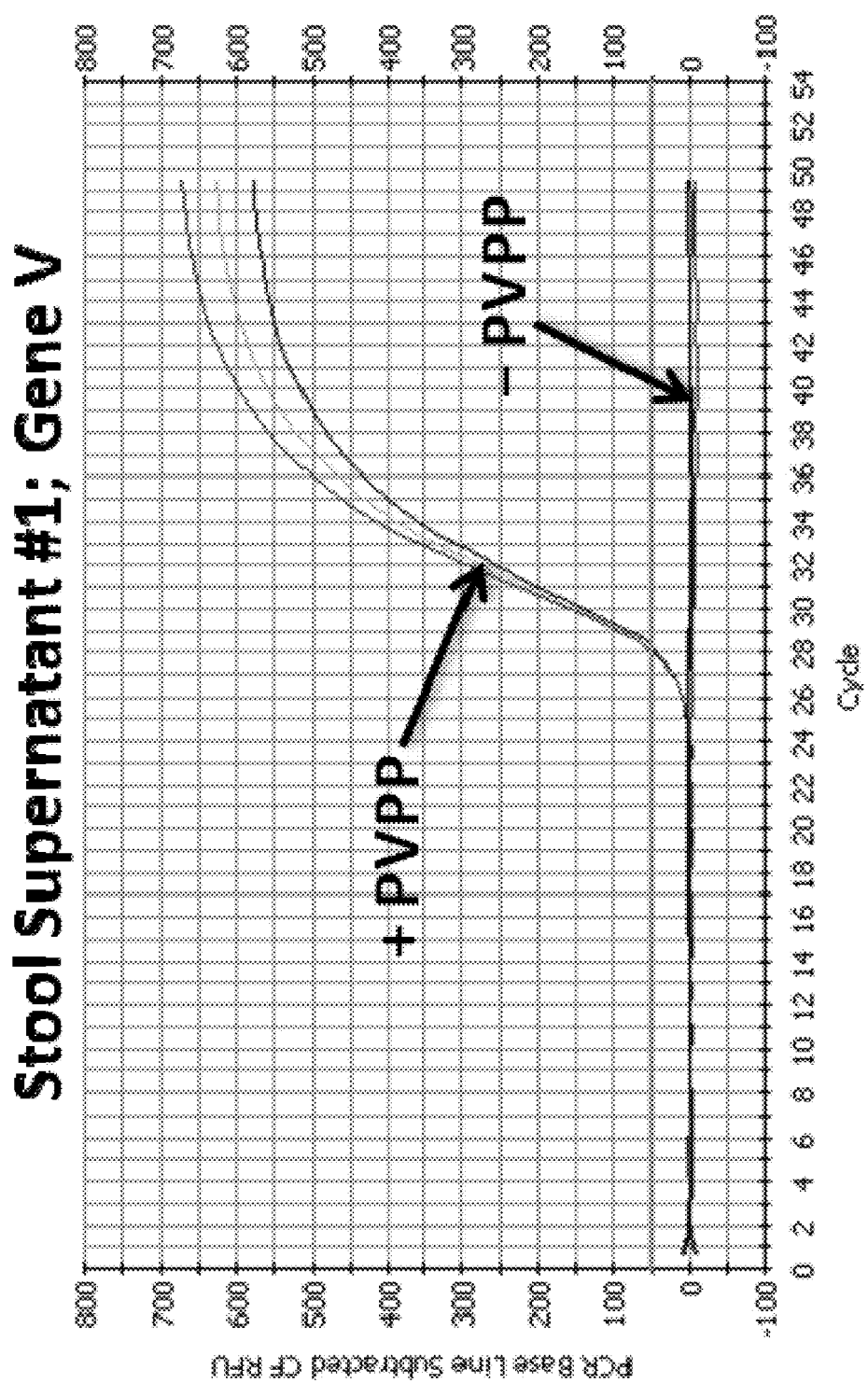
Figure 9D:
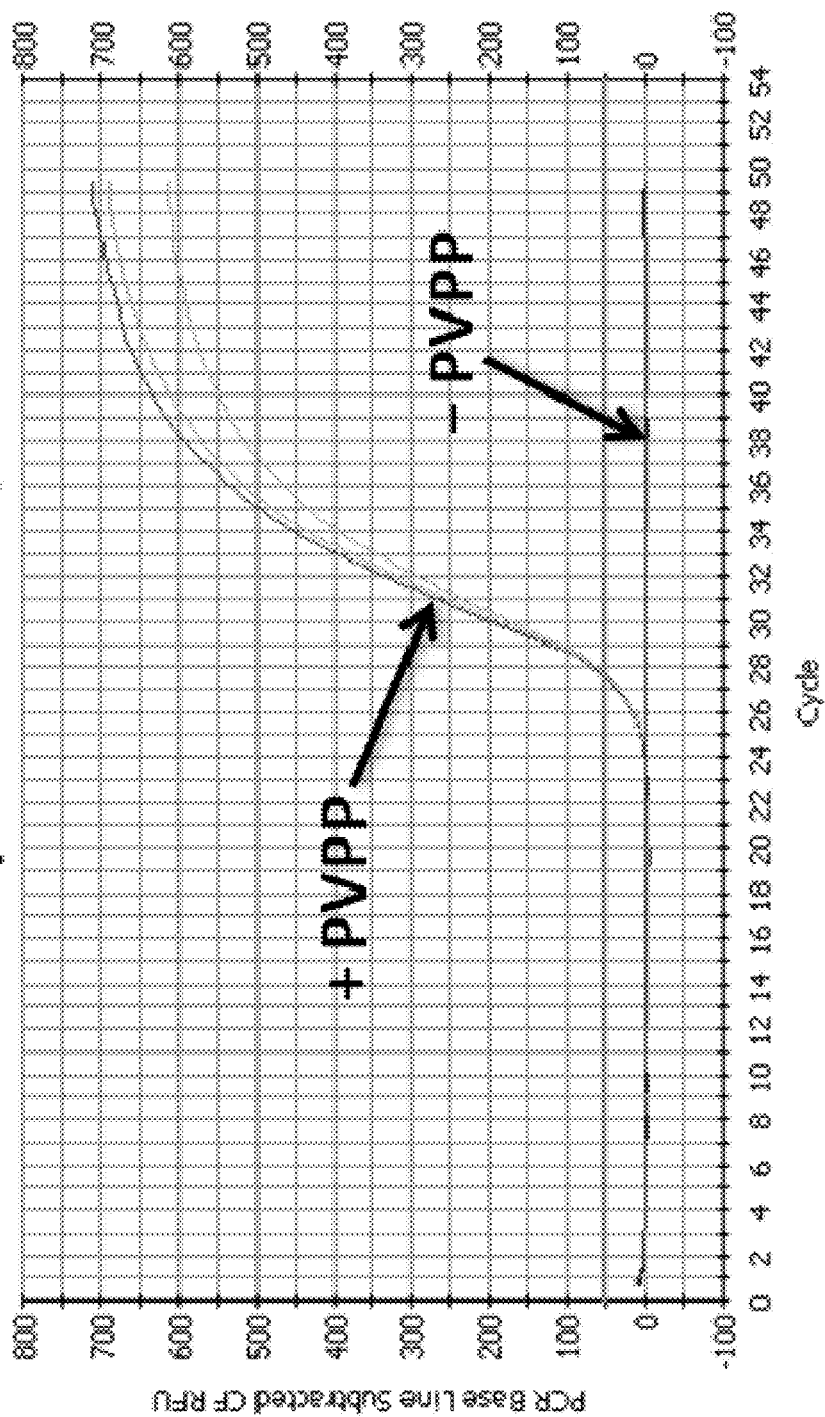

During the development of embodiments of the technology provided herein, it was demonstrated that PVP (e.g., PVPP) removes PCR inhibitors from a stool sample (see FIG. 9). Volumes of 20 milliliters were taken from the supernatants of two different stool supernatant samples. For each stool sample, one aliquot was treated with PVP and the other was left untreated. Otherwise, the samples were processed identically to capture two different nucleic acid targets (FIG. 9, Gene A and Gene V). After capture and final elution, the recoveries of the two targets were monitored by a SYBR Green quantitative PCR (qPCR) assay using 1 microliter of eluate in a 25 microliter reaction volume. For both targets from both stool supernatants, aliquots treated with PVP were amplified whereas the untreated aliquots failed to produce any qPCR signal. These results demonstrate the necessity and efficacy of PVP as an inhibitor-removal treatment when extracting DNA from stool samples for assay by a quantitative PCR assay.

Example 2

During the development of embodiments of the technology provided herein, data were collected demonstrating that spin filtering improves the removal of PCR inhibitors. The experiment compared PVP (e.g., PVPP) of different sizes for the ability to remove PCR inhibitors from stool supernatant samples. Two commercially available PVP compositions were compared: Polyclar® 10 and Polyplasdone® XL, which are composed of PVP particles having an average diameter of 30-50 micrometers and 100-130 micrometers, respectively. Inhibitor removal by the two PVP compositions was assessed by qPCR in which 1 microliter or 5 microliters of the isolated DNA eluates were used in a 25-microliter reaction volume.

Figure 10B:
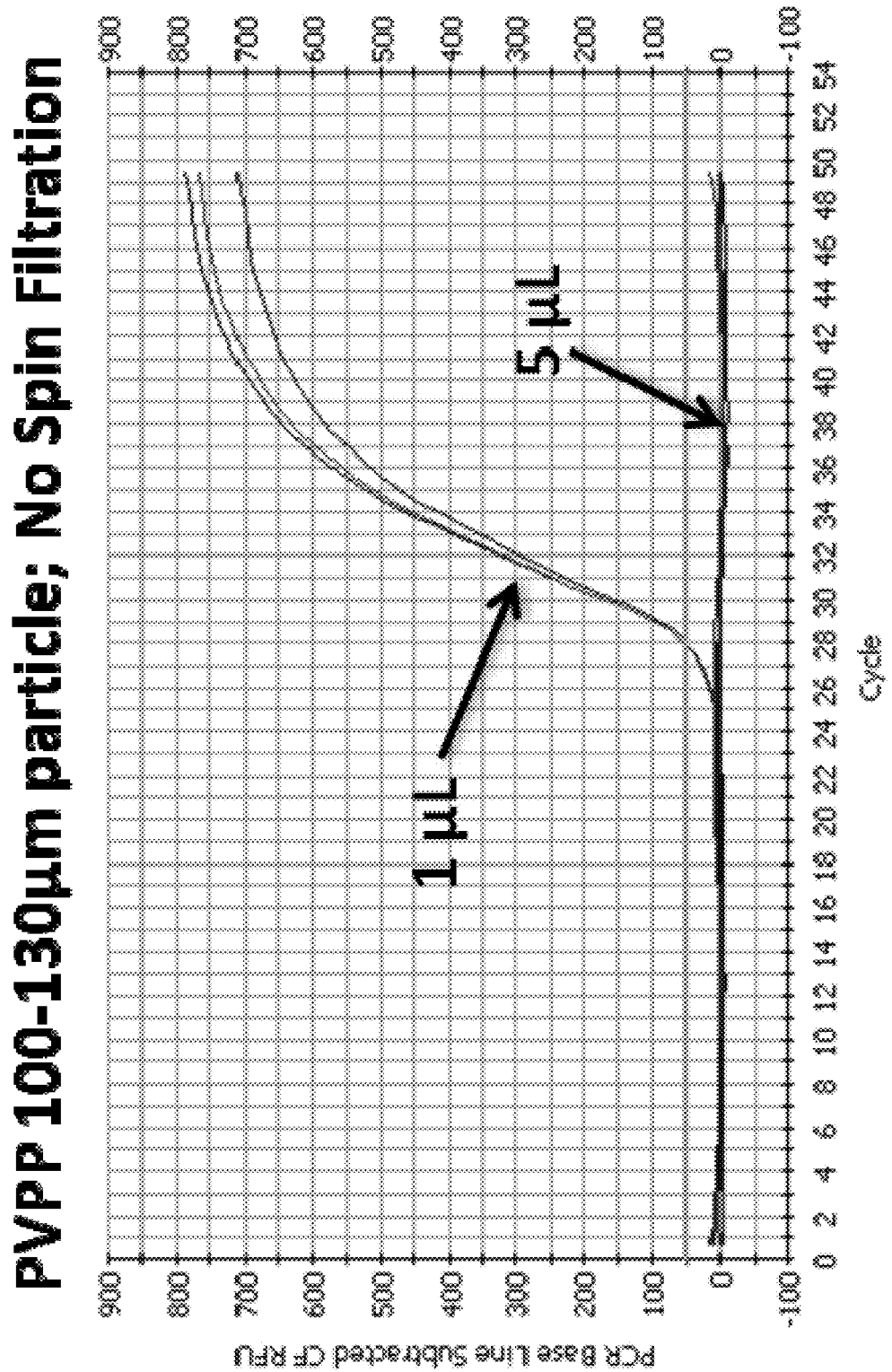

First, both types of PVP were separated from the stool supernatant by pelleting (centrifugation). For both PVP types, samples showed equal recovery and amplification curve shape when 1 microliter of eluted DNA was added to the qPCR. However, using 5 microliters of eluate failed to produce any qPCR signal, indicating that PCR inhibitors remained in the sample (see FIGS. 10A and 10B).

Figure 10C:
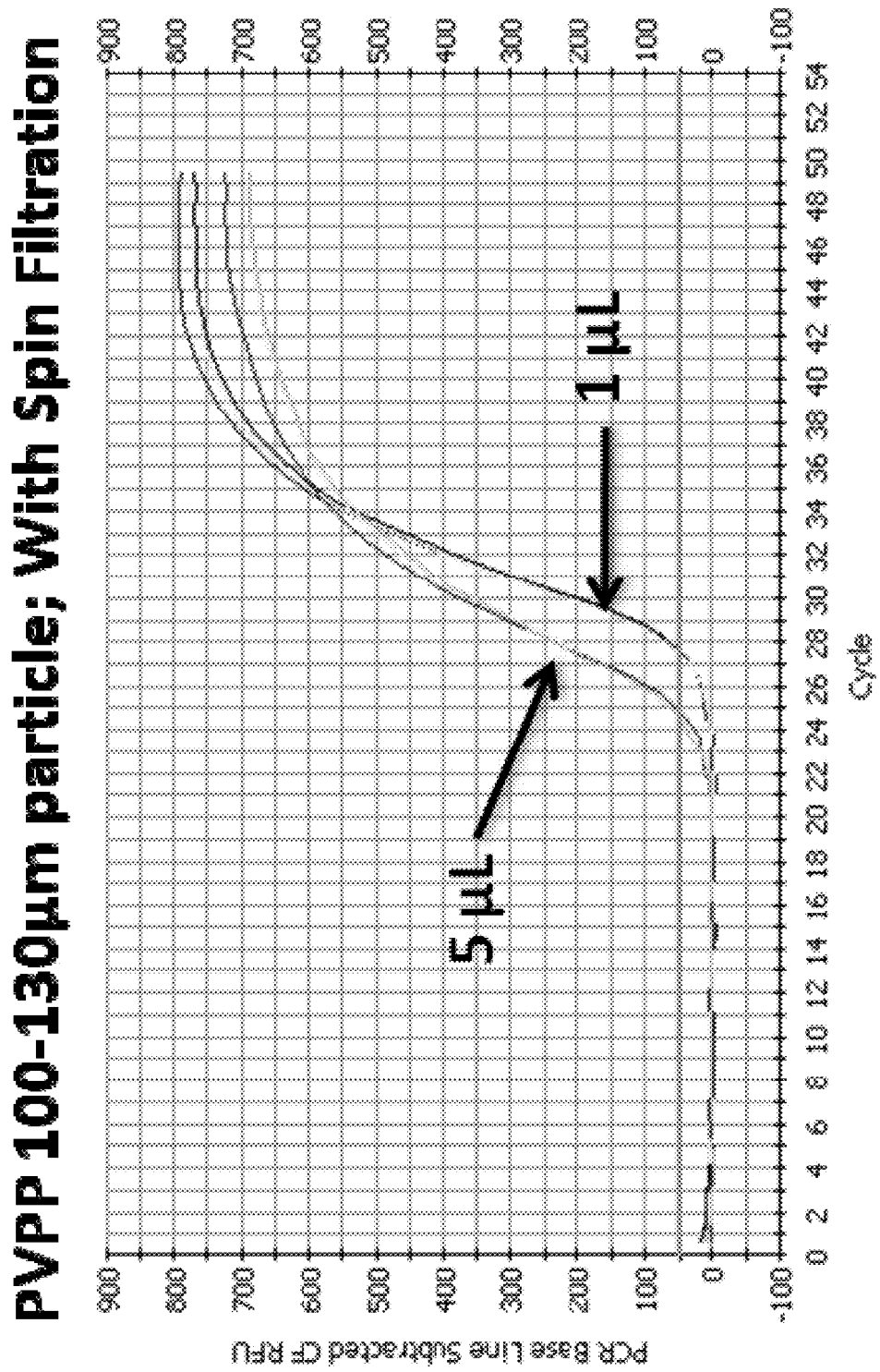
Figure 10D:
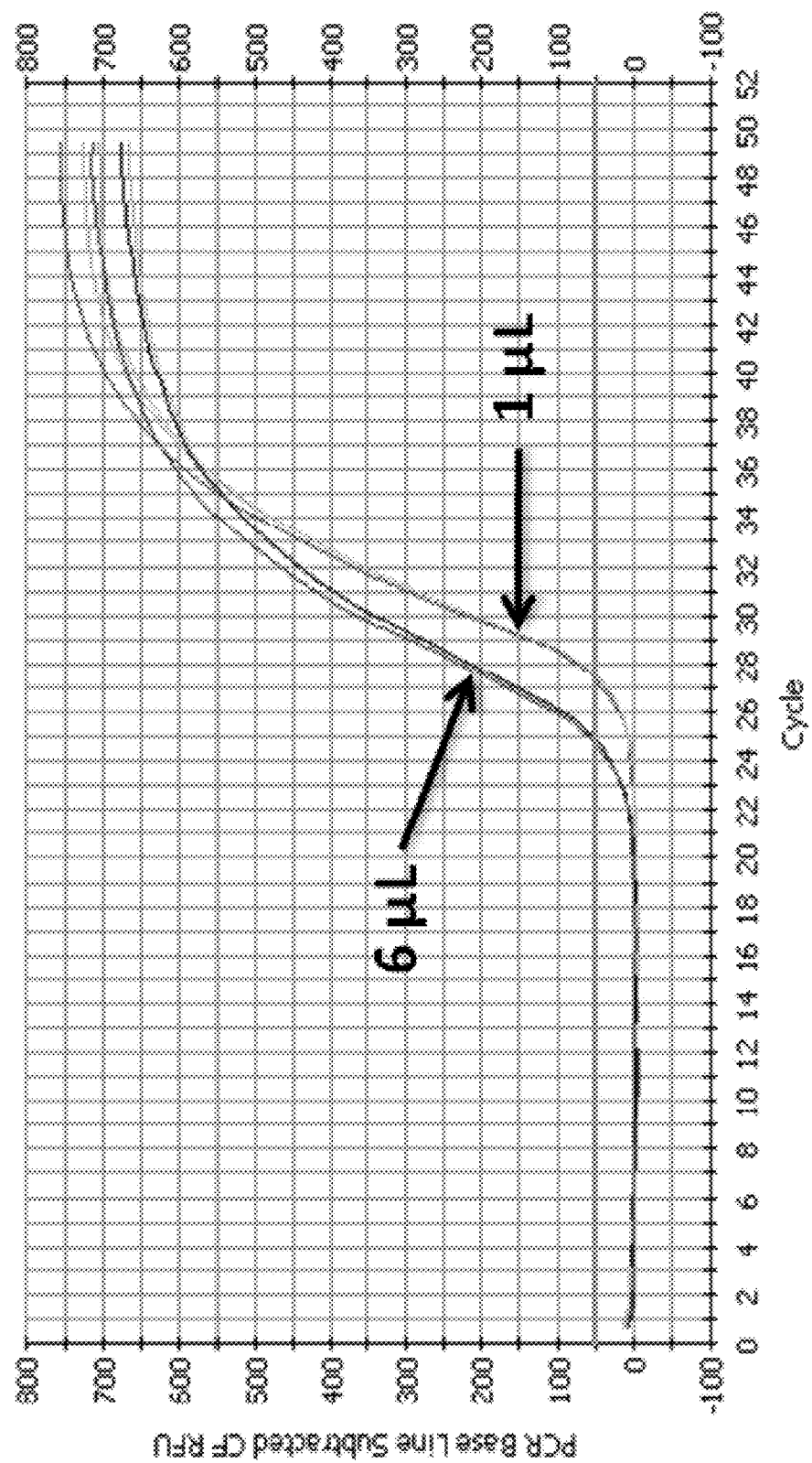

Next, spin column filtration was tried as an alternative method to separate the PVP from the stool supernatant. The smaller particle size PVP could not be processed in this manner as the PVP apparently packed down so tightly in the spin column that the liquid stool supernatant could not pass through. However, the larger particle size PVP did not have this same problem and the sample preparation could easily be spin filtered. The spin column contained a polyethylene frit (20-micrometer nominal pore size) to collect the PVP. When separating the large particle PVP from the stool supernatant via spin column filtration equipped with a polyethylene frit, the eluate volume in the qPCR could be increased to 5 microliters or 6 microliters without obvious inhibition (see FIGS. 10C and 10D). As shown in Table 1, when using 5 or 6 microliters of eluate, the calculated strand number was approximately five or six times the calculated strand number when using 1 microliter of eluate. These results demonstrate the benefits of PVP treatment plus spin column filtration for removal of PCR inhibitors from stool samples.

TABLE 1

| Treatment | Volume | Strands | % Expected |
|---|---|---|---|
| PVPP 30-50 | 1 μL | 950 | |
| No spin filter | 5 μL | No Signal (complete inhibition) | 0 |
| PVPP 100-130 | 1 μL | 907 | |
| No spin filter | 5 μL | No Signal (complete inhibition) | 0 |
| PVPP 100-130 With spin filter | 1 μL 5 μL | 1136 6751 | 119 |
| PVPP 100-130 With spin filter | 1 μL 6 μL | 3110 18600 | 99.68 |

Example 3

During the development of embodiments of the technology provided herein, experiments were performed to compare the localization efficiencies of the conventional technology (e.g., a Promega PolyA Tract backed with a 1-inch outer diameter×one-eighth-inch thick N52 neodymium magnet) and the magnetic microparticle localizing device of Light and Miller (grade N52 neodymium magnets in the S-N configuration) for samples of low (i.e., 1 centipoise) and high (i.e., 25 centipoise) viscosities.

Test solutions of the appropriate viscosity (e.g., 1 or 25 centipoise) were placed in a conventional device or an embodiment of the technology provided herein for testing. Samples were exposed to the magnetic field, the liquid was aspirated at the time intervals indicated for each sample, and the particles remaining in suspension were quantified by spectrometry. A decrease in absorbance indicates a decreased concentration of microparticles suspended in solution (i.e., more particles localized and removed from suspension by magnetic separation). Results for the conventional technology are provided below in FIG. 11A. Results for the magnetic microparticle localization device are provided in FIG. 11B. In FIGS. 11A and B, data collected for the 25 centipoise solution are shown with squares (■) and data collected for the 1 centipoise solution are shown with diamonds (♦).

Example 4

Figures 12A, 12B:
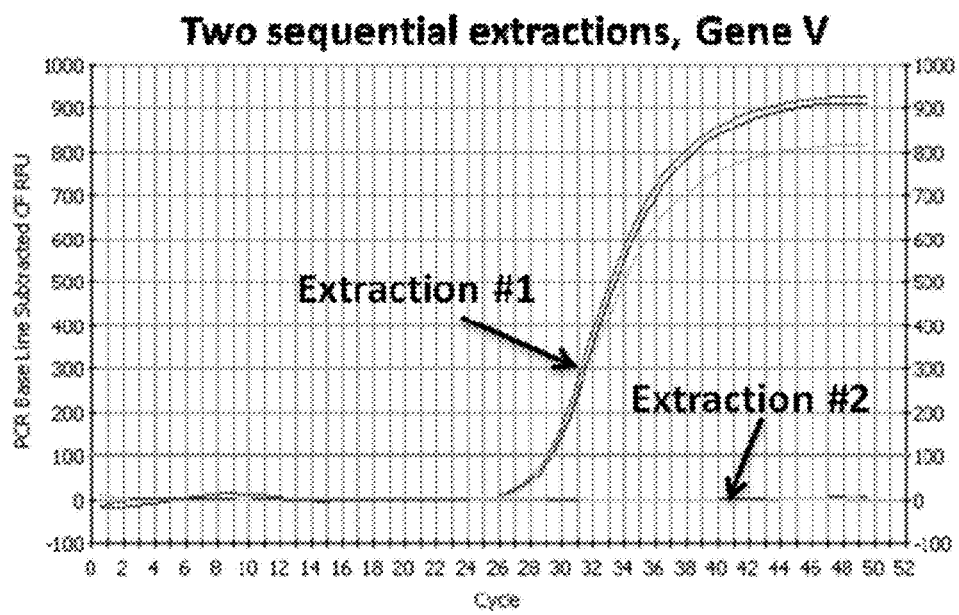
FIGS. 12A-B.

During the development of embodiments of the technology provided herein, it was demonstrated that the majority of the DNA for a given target is depleted from a stool supernatant in a single extraction. The extraction was performed according to the flow chart shown in FIG. 1. After final elution, the recoveries of the two targets (Gene A and Gene V) from extractions 1 and 2 were monitored by SYBR Green qPCR assays using 1 microliter of eluate in a 25-microliter volume reaction. For both targets, extraction 1 yielded good recovery of target, whereas the eluate from extraction 2 failed to produce any qPCR signal for either target (FIG. 12).

Example 5

Figure 13A:
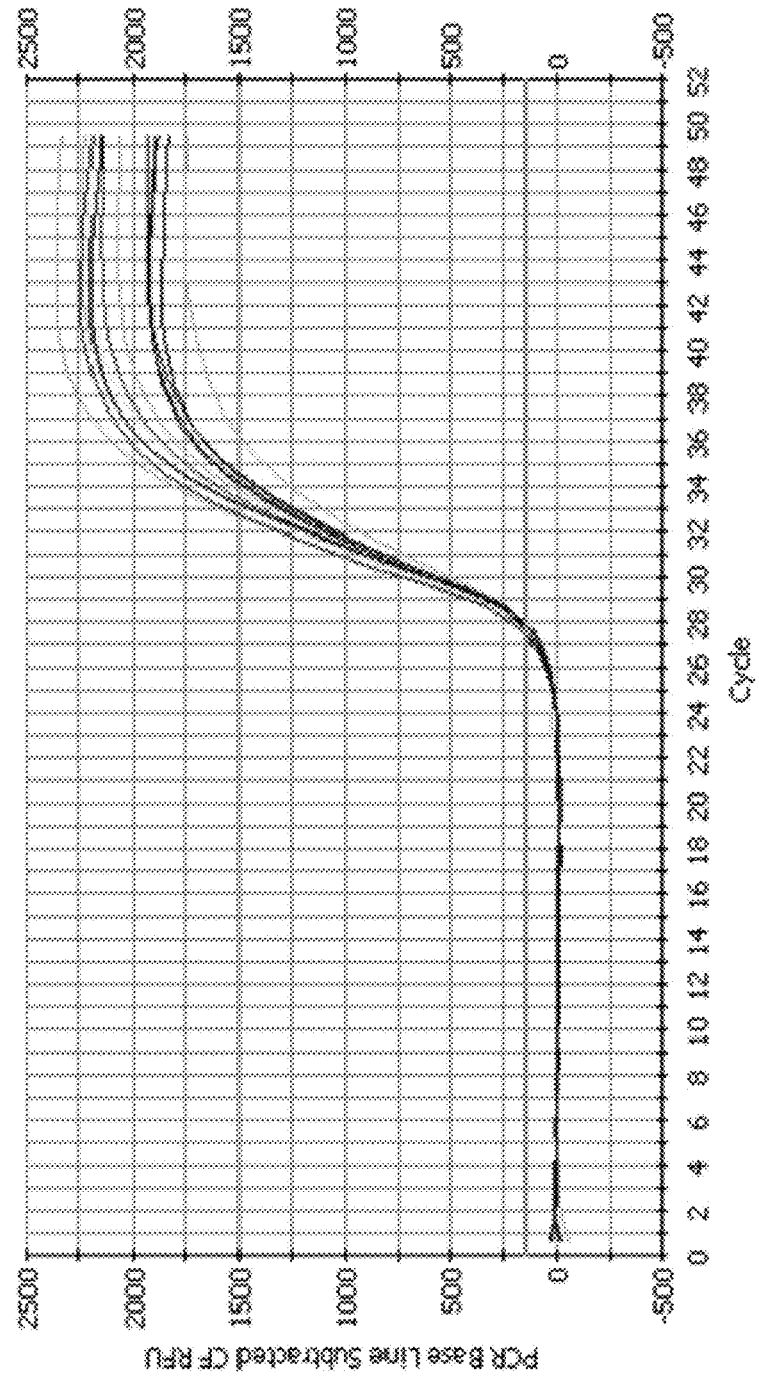
Figure 13C:
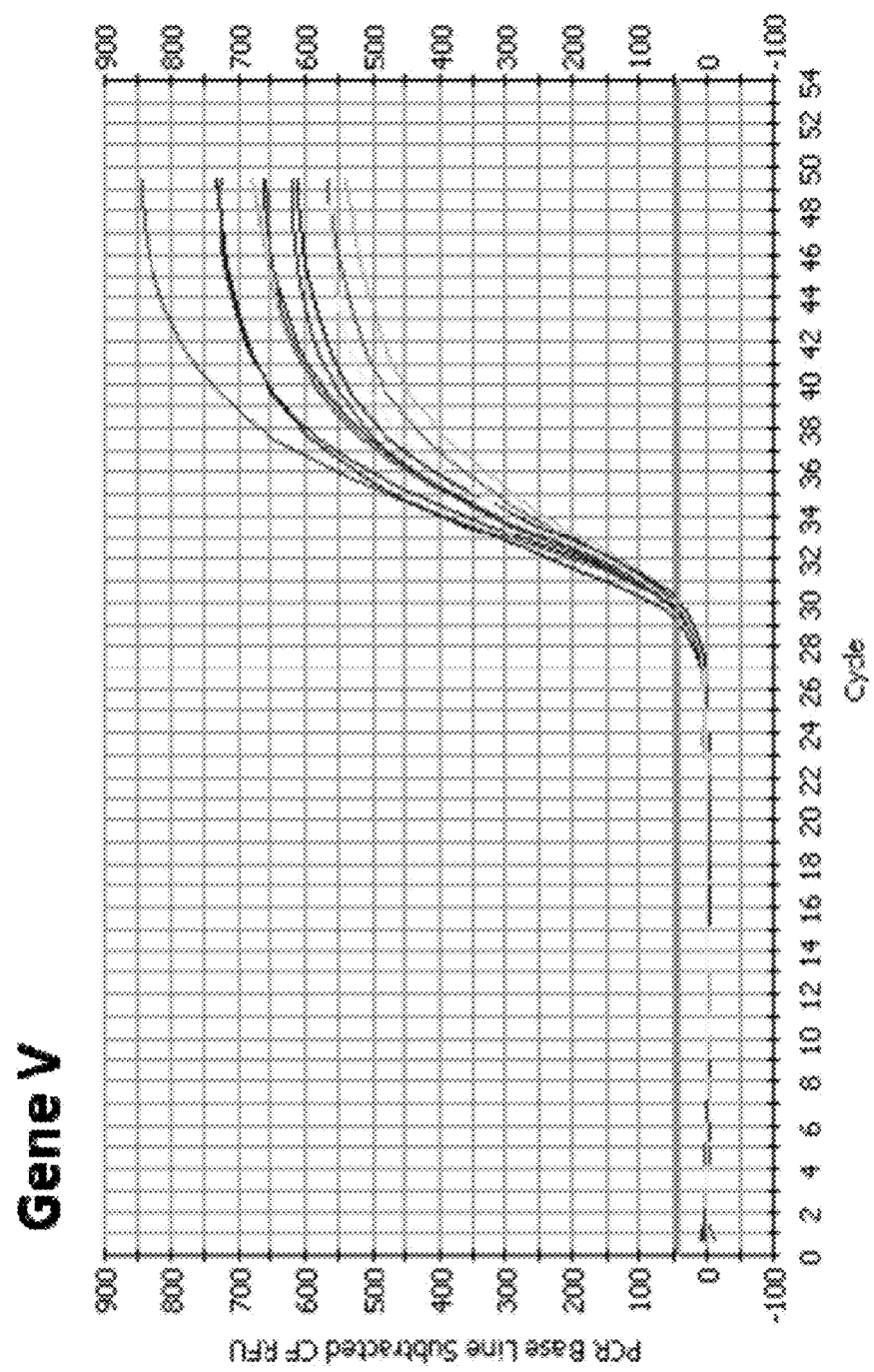
Figure 13D:
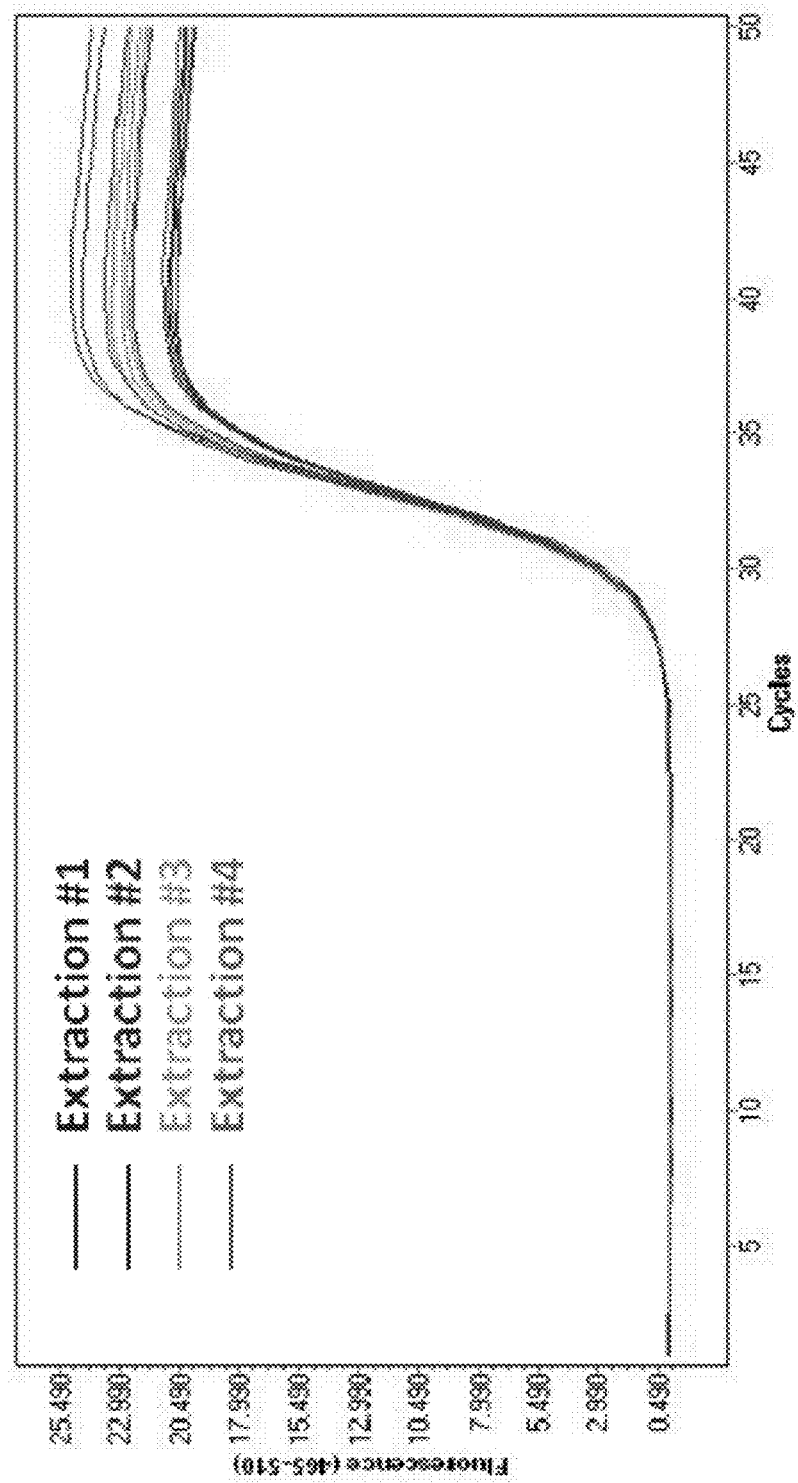

During the development of embodiments of the technology provided herein, it was demonstrated that DNA extraction can be performed repeatedly on a single sample through a minimum of four cycles of denaturation/hybridization without compromising the integrity of the human DNA in the stool supernatant. In this example, four targets (Genes A, F, V, and W) were captured from the sample and the order of their capture was varied. After elution, the recovery of each target was monitored by SYBR Green qPCR. In FIG. 13, plots show the amplification curves for each gene when it was captured first, second, third, and fourth in the extraction sequence. The superposition of the amplification curves demonstrates that recoveries were approximately equal regardless of the order of extraction. Table 3 quantifies the results from FIG. 13.

TABLE 3

| Target | Extraction | Mean $C_p$ | Mean Strands/μL |
|---|---|---|---|
| Gene A | #1 | 28.92 | 862 |
|  | #2 | 28.89 | 878 |
|  | #3 | 28.85 | 907 |
|  | #4 | 28.73 | 984 |
| Gene F | #1 | 29.32 | 499 |
|  | #2 | 29.36 | 489 |
|  | #3 | 29.29 | 511 |
|  | #4 | 29.01 | 614 |
| Gene V | #1 | 31.29 | 129 |
|  | #2 | 31.01 | 155 |
|  | #3 | 31.18 | 139 |
|  | #4 | 30.84 | 177 |
| Gene W | #1 | 29.17 | 724 |
|  | #2 | 29.11 | 757 |
|  | #3 | 28.99 | 819 |
|  | #4 | 29.16 | 730 |

For all four genes, the mean $C_p$ (Crossing point—the cycle number at which the amplification curve crosses a fixed threshold) and strand numbers were essentially equal regardless of the order of extraction.

Example 6

Exemplary Procedure for Serial Isolation of a Plurality of Target Nucleic acids:

As diagrammed in FIG. 1:

1. A stool sample is homogenized, e.g., with a buffer, to form a stool homogenate. The homogenate treated to partition residual solids from the fluid, e.g., by centrifugation or filtration, to produce a "stool supernatant."
2. Stool supernatant is treated to remove assay inhibitors (e.g., with polyvinylpolypyrrolidone, as described in U.S. Pat. Appl. Ser. No. 61/485,338, which is incorporated herein by reference in its entirety), producing "clarified supernatant".
3. Ten milliliters of clarified supernatant (representing an equivalent of approximately 4 grams of stool) is mixed with guanidine thiocyanate (GTC) to a final concentration of 2.4 M;
4. The mixture is then heated in a 90° C. water bath for 10 minutes to denature the DNA (and proteins) present in the stool.
5. Paramagnetic particles containing covalently attached (coupled) oligonucleotides complementary to the target sequence(s) of interest ("target-specific capture probes") are added to the sample. The sample is then incubated (e.g., at ambient temperature, about 22-25° C.) for one hour to enable hybridization of the target DNA to the capture probes on the magnetic particles.
6. The mixture of clarified supernatant, GTC, and particles is exposed to a magnetic field to separate the particles (now containing target DNA hybridized to the capture probes) from the stool supernatant/GTC mixture, which is transferred to a new tube. See, e.g., U.S. patent application Ser. No. 13/089,116, which is incorporated herein by reference.
7. The paramagnetic particles are then washed and the target DNA eluted, ready for use in detection assays.
8. The supernatant/GTC mixture retained in step 6 is returned to the 90° C. water bath for 10 minutes to repeat denaturation (step 4). Step 5 is then repeated by adding magnetic particles containing capture probes complementary to different targets DNAs, and the hybridization, particle separation and elution steps are repeated to produce a purified sample of a second DNA target.

The denaturation/hybridization/separation cycle (steps 4-6) can be repeated at least four or more times to serially extract different target DNAs from the same stool supernatant sample.

Example 7

During the development of embodiments of the technology provided herein, the methods were tested in a clinical application. The following provides an example of workflow using the systems and methods of the present invention.

Study Design

This study was based on well-characterized archival stools from multiple medical centers, including referral centers and community medical centers in the United States and Denmark. Approval by institutional review boards was obtained. Stools were procured from case patients with proven colorectal cancer (CRC), cases with at least one colorectal adenoma≥1 centimeter, and age and sex matched control patients without neoplasia as assessed by colonoscopy. Patients had been recruited from both clinical and screening settings, and some were symptomatic. Those with known cancer syndromes or inflammatory bowel disease were excluded. Nearly 700 samples were tested, of which 133 were adenomas≥1 centimeter and 252 were cancer patients.

A multi-marker stool test was performed that included four methylated genes (vimentin, NDRG4, BMP3, and TFPI2), mutant KRAS, a reference gene beta-actin (ACTI), and hemoglobin. To evaluate test performance, case and control stools were distributed in balanced fashion to two different test sites; all assays were run by blinded technicians.

Stool Collection and Storage.

Prior to colonoscopy, which served as the gold standard, whole stools were collected in plastic buckets. A preservative buffer was added to the stool and buffered stools were archived at −80° C. However, the timing of buffer addition, duration between defecation and freezing, and whether or not samples were homogenized prior to storage were not standardized and varied across participating centers.

Marker Selection.

Candidate genes were identified that individually or in combinations (e.g., KRAS+BMP3+NDRG4+IFPI12+vimentin+reference and/or ACTB+hemoglobin) yielded nearly complete separation of colorectal neoplasia from normal mucosa. Four methylated gene markers emerged as the most discriminant—NDRG4, BMP3, vimentin, and TFPI2. Mutant KRAS and hemoglobin detection complement methylated gene markers detected in stool and, accordingly, were also evaluated in the marker panel. Finally, assay of the reference gene beta-actin (ACTB) was used to determine total human genome equivalents in stool and, as human DNA levels in stool increase with colorectal neoplasia, to serve as a candidate marker itself.

Stool Processing and Target Gene Capture

Promptly after thawing, buffered stools were thoroughly homogenized and centrifuged. A 14-milliliter aliquot of stool supernatant was then treated with polyvinylpolypyrrolidone at a concentration of 50 milligrams per milliliter. Direct capture of target gene sequences by hybridization with oligonucleotide probes was performed on supernatant material. Briefly, 10 milliliters of insoluble PVP-treated supernatant was denatured in 2.4 M guanidine isothiocyanate (Sigma, St. Louis Mo.) at 90° C. for 10 minutes; 300-500 micrograms of Sera-Mag carboxylate modified beads (ThermoFisher Scientific, Waltham Mass.) functionalized with each oligonucleotide capture probe were subsequently added to denatured stool supernatant and incubated at room temperature for one hour. Sera-Mag beads were collected on a magnetic rack and washed three times using MOPS washing buffer (10 mM MOPS; 150 mM NaCl, pH 7.5), and then eluted in 60 microliters of nuclease free water with 20 nanograms per microliter tRNA (Sigma). In this study, four selected methylated markers, vimentin, NDRG4, BMP3, and TFPI2, and one reference gene ACTB, were captured together in one hybridization reaction; the mutation marker KRAS was subsequently captured in another hybridization reaction. The capture probes used, shown here with their 5'-six carbon amino modified linkage (Integrated DNA Technology, Coralville, Iowa), were as follows:

```
for vimentin:
                                        (SEQ ID NO: 1)
/5AmMC6/CTGTAGGTGCGGGTGGACGTAGTCACGTAGCTCCGGCTGG

A-3';

for NDRG4:
                                        (SEQ ID NO: 2)
/5AmMC6/TCCCTCGCGCGTGGCTTCCGCCTTCTGCGCGGCTGGGGTG

CCCGGTGG-3';

for BMP3:
                                        (SEQ ID NO: 3)
/5AmMC6/GCGGGACACTCCGAAGGCGCAAGGAG-3';

for TFPI2:
                                        (SEQ ID NO: 4)
/5AmMC6/CGCCTGGAGCAGAAAGCCGCGCACCT-3';

for ACTB:
                                        (SEQ ID NO: 5)
/5AmMC6/CCTTGTCACACGAGCCAGTGTTAGTACCTACACC-3';

for KRAS:
                                        (SEQ ID NO: 6)
/5AmMC6/GGCCTGCTGAAAATGACTGAATATAAACTTGTGGTAGTTG GAGC-3';
and (SEQ ID NO: 7)
/5AmMC6/CTCTATTGTTGGATCATATTCGTCCACAAAATGATTCTGAA

TTAGC-3'
```

Methylation Assays.

Methylated markers were quantified by the QuARTS method, as we have previously described (see, e.g., U.S. patent application Ser. Nos. 12/946,737; 12/946,745; and Ser. No. 12/946,752, incorporated herein by reference in their entireties for all purposes). This method combines a polymerase-based target DNA amplification process with an invasive cleavage-based signal amplification process. We treated 45 microliters of captured DNA with bisulfite using the EZ-96 DNA Methylation Kit (Zymo Research, Irvine Calif.) and eluted the sample in 50 microliters of 10 mM Tris, 0.1 mM EDTA pH 8.0 with 20 nanograms per microliter tRNA (Sigma) on a 96-well PCR plate; 10 microliters of bisulfite-treated DNA was assayed with the QuARTS method in 30-microliter reaction volumes on a 96-well PCR plate. PCR plates were cycled in a LightCycler 480 (Roche).

Two separate triplex QuARTS assays were designed to detect the methylated markers vimentin, NDRG4, BMP3, and TFPI2 using ACTB as a reference gene for each. The first triplex assay contained ACTB, vimentin, and NDRG4, and the second contained ACTB, BMP3, and TFPI2. Each QuARTS reaction incorporated 400-600 nM primers and detection probes, 100 nM invasive oligonucleotide, 600-700 nM each of FAM (Hologic, Madison Wis.), Yellow (Hologic), and Quasor 670 (BioSearch Technologies, Novato Calif.) fluorescence resonance energy transfer reporter cassettes (FRETs), 6.675 nanogram per microliter Cleavase 2.0 (Hologic), 1 unit hot-start GoTaq DNA polymerase (Promega, Madison Wis.), 10 mM MOPS, 7.5 mM $MgCl_2$, and 250 μM each dNTP. QuARTS cycling conditions consisted of 95° C. for 3 minutes, then 10 cycles each comprising 95° C. for 20 seconds, 67° C. for 30 seconds, and 70° C. for 30 seconds, followed by 45 cycles each comprising 95° C. for 20 seconds, 53° C. for 1 minute, and 70° C. for 30 seconds, and finally a 30-second hold at 40° C. For each target below, the two methylation-specific primers and probe (Integrated DNA Technology, Coralville, Iowa) were as follows:

```
For vimentin:
Primer
                                        (SEQ ID NO: 8)
5'-GGC GGT TCG GGT ATC G-3', Primer
                                        (SEQ ID NO: 9)
5'-CGT AAT CAC GTA ACT CCG AC T-3', Probe
                                        (SEQ ID NO: 10)
5'-GAC GCG GAG GCG ACT CGG TCG/3'C6/;

for NDRG4:
Primer
                                        (SEQ ID NO: 11)
5'-CGG TTT TCG TTC GTT TTT TCG-3', Primer
                                        (SEQ ID NO: 12)
5'-GTA ACT TCC GCC TTC TAC GC-3', Probe
                                        (SEQ ID NO: 13)
5'-CGC CGA GGG TTC GTT TAT CG/3'C6/;

for BMP3:
Primer
                                        (SEQ ID NO: 14)
5'-GTT TAA TTT TCG GTT TCG TCG TC-3', Primer
                                        (SEQ ID NO: 15)
5'-CTC CCG ACG TCG CTA CG-3', Probe
                                        (SEQ ID NO: 16)
5'-CGC CGA GGC GGT TTT TTG CG/3'C6/;
and for TPFI2:
Primer
                                        (SEQ ID NO: 17)
5'-TCG TTG GGT AAG GCG TTC-3',
```

```
Primer
                                          (SEQ ID NO: 18)
5'-AAA CGA ACA CCC GAA CCG-3', Probe
                                          (SEQ ID NO: 19)
5'-GAC GCG GAG GCG GTT TTT TGT T/3'C6/.
```

The TFPI2 assay had a specific invasive oligonucleotide:

```
                                          (SEQ ID NO: 20)
             5'-GCG GGA GGA GGT GCC-3'.
```

Primers and probe for detecting bisulfite-treated ACTB were:

```
Primer
                                          (SEQ ID NO: 21)
5'-TTT GTT TTT TTG ATT AGG TGT TTA AGA-3', Primer
                                          (SEQ ID NO: 22)
5'-CAC CAA CCT CAT AAC CTT ATC-3', Probe
                                          (SEQ ID NO: 23)
5'-CCA CGG ACG ATA GTG TTG TGG/3'C6/.
```

Each plate included bisulfite-treated DNA samples, standard curve samples, positive and negative controls, and water blanks. Standard curves were made using 300 to 1000 target sequences cut from engineered plasmids. Bisulfite-treated CpGenome universal methylated DNA (Millipore, Billerica, Mass.) and human genomic DNA (Merck, Germany) were used as positive and negative controls. DNA strand number was determined by comparing the $C_p$ of the target gene to the standard curve for the relevant assay. Percent methylation for each marker was determined by dividing the strand number of the methylated gene by the ACTB strand number and multiplying by 100.

KRAS Mutation

The KRAS gene was first PCR amplified with primers flanking codons 12/13 using 10 microliters of captured KRAS DNA as template. PCR was conducted with 1× LightCycler®480 SYBR Green I Master (Roche, Germany) and 200 nM each primer. Cycling conditions were 95° C. for 3 minutes, followed by 15 cycles each at 95° C. for 20 seconds, 62° C. for 30 seconds, and 72° C. for 30 seconds. Primer sequences were:

```
                                          (SEQ ID NO: 24)
    5'-AGG CCT GCT GAA AAT GAC TG-3',
    and (SEQ ID NO: 25)
    5'-CTA TTG TTG GAT CAT ATT CG TC-3'.
```

Each amplified sample was diluted 500-fold in nuclease free water. A 10-microliter aliquot of the 500-fold sample dilutions was added to a 96-well PCR plate with an automated liquid handler (epMotion, Eppendorf, Hauppauge N.Y.). QuARTS assays were then used to evaluate seven mutations at codons 12/13 of the KRAS gene. Each mutation assay was designed as a singleplex assay. KRAS mutation-specific forward primers and probes were:

```
for G12S mutation:
Primer
                                          (SEQ ID NO: 26)
5'-CTT GTG GTA GTT GGA GCA A-3'

Probe
                                          (SEQ ID NO: 27)
5'-GCG CGT CCA GTG GCG TAG GC/3'C6/;

for G12C mutation
Primer
                                          (SEQ ID NO: 28)
5'-AAA CTT GTG GTA GTT GGA CCT T-3'

Probe
                                          (SEQ ID NO: 29)
5'-GCG CGT CCT GTG GCG TAG GC/3'C6/;

for G12D mutation
Primer
                                          (SEQ ID NO: 30)
5'-TAT AAA CTT GTG GTA GTT GGA CCT C-3'

Probe
                                          (SEQ ID NO: 31)
5'-GCG CGT CCC GTG GCG TAG GC/3'C6/;

for G12D mutation
Primer
                                          (SEQ ID NO: 32)
5'-ACT TGT GGT AGT TGG AGC TCA-3'

Probe
                                          (SEQ ID NO: 33)
5'-GCG CGT CCA TGG CGT AGG CA/3'C6/;

for G12V mutation
Primer
                                          (SEQ ID NO: 34)
5'-ACT TGT GGT AGT TGG AGC TCT-3'

Probe
                                          (SEQ ID NO: 35)
5'-GCG CGT CCT TGG CGT AGG CA/3'C6/;

for G12A mutation
Primer
                                          (SEQ ID NO: 36)
5'-AAC TTG TGG TAG TTG GAG ATG C-3'

Probe
                                          (SEQ ID NO: 37)
5'-GCG CGT CCC TGG CGT AGG CA/3'C6/;

for G13D mutation
Primer
                                          (SEQ ID NO: 38)
5'-GGT AGT TGG AGC TGG TCA-3'

Probe
                                          (SEQ ID NO: 39)
5'-GCG CGT CCA CGT AGG CAA GA/3'C6/.
```

For all KRAS mutants, the reverse primer used is

```
                                          (SEQ ID NO: 40)
       5'-CTA TTG TTG GAT CAT ATT CGT C-3'.
```

QuARTS cycling conditions and reagent concentrations for KRAS were the same as those in the methylation assays. Each plate contained standards made of engineered plasmids, positive and negative controls, and water blanks, and was run in a LightCycler 480 (Roche). DNA strand number was determined by comparing the $C_p$ of the target gene to the standard curve for that assay. The concentration of each mutation marker in 50 microliters of KRAS was calculated based on the 500-fold dilution factor and an amplification efficiency of 1.95. This value was divided by the ACTB concentration in the methylation assay and then multiplied by 100 to determine the percent mutation.

Hemoglobin Assay.

To quantify hemoglobin in stool, the semi-automated HemoQuant test was performed on two buffered stool aliquots (each normalized to 16 milligrams of stool) per patient, as described in Ahlquist, et al. ("HemoQuant, a new quantitative assay for fecal hemoglobin. Comparison with Hemoccult". Ann Intern Med 101:297-302 (1984)). This test allowed assessment of the complementary value of fecal hemoglobin.

Data Analysis

Using the combination of sample processing methods described herein, comprising inhibitor removal and target capture purification, combined with the methylation and mutation markers described, the present study of 678 samples achieved the following sensitivity levels: 63.8% sensitivity for adenoma detection and 85.3% sensitivity for colorectal cancer at a specificity level of 90%.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described.

Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

---

We claim:

1. A method for isolating a human target DNA from a fluid fraction prepared from human stool homogenate for use in a nucleic acid detection reaction, the method comprising:
   i) treating a fluid fraction from a human stool homogenate with insoluble polyvinylpyrrolidone to bind inhibitor, if present, in an insoluble inhibitor complex, to produce a treated stool fluid;
   ii) exposing the treated stool fluid to a target sequence-specific capture reagent comprising particles attached to oligonucleotides complementary to at least a portion of human target DNA, under conditions wherein the target sequence-specific capture reagent forms a target sequence-specific capture reagent/human target DNA capture complex,
   iii) separating the capture complex from said treated stool fluid;
   iv) recovering human target DNA from the capture complex in a human target DNA solution; and
   v) performing a DNA detection reaction on said human target DNA solution.

2. The method of claim 1, further comprising:
   vi) retaining residual treated stool fluid after said separating said capture complex in iii); and
   vii) repeating the exposing, separating, and recovering of steps ii) to iv) using the residual treated stool fluid and a second target sequence-specific capture reagent that is specific for a second human target DNA.

3. The method of claim 1, wherein said insoluble polyvinylpyrrolidone is provided as a capsule or pressed tablet comprising a premeasured amount of insoluble polyvinylpyrrolidone.

4. The method of claim 1, wherein treating said fluid fraction from a human stool homogenate with insoluble polyvinylpyrrolidone to produce said treated stool fluid comprises passing treated stool fluid through porous filtering material, wherein the insoluble inhibitor complex is retained by the porous filtering material.

5. The method of claim 1, wherein said particle of said target-specific capture reagent comprises a magnetic particle and wherein said separating said capture complex comprises exposing said capture complex to a magnetic field.

6. The method of claim 1, wherein recovering said human target DNA comprises eluting said human target DNA from said capture complex.

7. The method of claim 1, wherein said nucleic acid detection reaction comprises use of at least one enzyme selected from the group consisting of a restriction endonuclease, a flap endonuclease, a reverse transcriptase, a ligase, an RNA polymerase, and a DNA polymerase.

8. The method of claim 7, wherein said nucleic acid detection reaction comprises a polymerase chain reaction.

* * * * *

SEQUENCE LISTING

```
<160> NUMBER OF SEQ ID NOS: 40

<210> SEQ ID NO 1
<211> LENGTH: 41
<212> TYPE: DNA
<213> ORGANISM: Artificial Sequence
<220> FEATURE:
<223> OTHER INFORMATION: Synthetic

<400> SEQUENCE: 1
ctgtaggtgc gggtggacgt agtcacgtag ctccggctgg a                          41

<210> SEQ ID NO 2
<211> LENGTH: 48
<212> TYPE: DNA
<213> ORGANISM: Artificial Sequence
<220> FEATURE:
<223> OTHER INFORMATION: Synthetic

<400> SEQUENCE: 2
tccctcgcgc gtggcttccg ccttctgcgc ggctggggtg cccggtgg                   48

<210> SEQ ID NO 3
<211> LENGTH: 26
<212> TYPE: DNA
<213> ORGANISM: Artificial Sequence
<220> FEATURE:
<223> OTHER INFORMATION: Synthetic

<400> SEQUENCE: 3
gcgggacact ccgaaggcgc aaggag                                           26

<210> SEQ ID NO 4
<211> LENGTH: 26
<212> TYPE: DNA
<213> ORGANISM: Artificial Sequence
<220> FEATURE:
<223> OTHER INFORMATION: Synthetic

<400> SEQUENCE: 4
cgcctggagc agaaagccgc gcacct                                           26

<210> SEQ ID NO 5
<211> LENGTH: 34
<212> TYPE: DNA
<213> ORGANISM: Artificial Sequence
<220> FEATURE:
<223> OTHER INFORMATION: Synthetic
```

<400> SEQUENCE: 5
ccttgtcaca cgagccagtg ttagtaccta cacc                                      34

<210> SEQ ID NO 6
<211> LENGTH: 44
<212> TYPE: DNA
<213> ORGANISM: Artificial Sequence
<220> FEATURE:
<223> OTHER INFORMATION: Synthetic

<400> SEQUENCE: 6
ggcctgctga aaatgactga atataaactt gtggtagttg gagc                           44

<210> SEQ ID NO 7
<211> LENGTH: 46
<212> TYPE: DNA
<213> ORGANISM: Artificial Sequence
<220> FEATURE:
<223> OTHER INFORMATION: Synthetic

<400> SEQUENCE: 7
ctctattgtt ggatcatatt cgtccacaaa atgattctga attagc                         46

<210> SEQ ID NO 8
<211> LENGTH: 15
<212> TYPE: DNA
<213> ORGANISM: Artificial Sequence
<220> FEATURE:
<223> OTHER INFORMATION: Synthetic

<400> SEQUENCE: 8
ggcggttcgg gtatc                                                           15

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
cgtaatcacg taactccgac t                                                    21

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
gacgcggagg cgagtcggtc g                                                    21

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
cggttttcgt tcgttttttc g                                                    21

<210> SEQ ID NO 12

```
<211> LENGTH: 20
<212> TYPE: DNA
<213> ORGANISM: Artificial Sequence
<220> FEATURE:
<223> OTHER INFORMATION: Synthetic

<400> SEQUENCE: 12
gtaacttccg ccttctacgc                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
cgccgagggt tcgtttatcg                                               20

<210> SEQ ID NO 14
<211> LENGTH: 23
<212> TYPE: DNA
<213> ORGANISM: Artificial Sequence
<220> FEATURE:
<223> OTHER INFORMATION: Synthetic

<400> SEQUENCE: 14
gtttaatttt cggtttcgtc gtc                                           23

<210> SEQ ID NO 15
<211> LENGTH: 17
<212> TYPE: DNA
<213> ORGANISM: Artificial Sequence
<220> FEATURE:
<223> OTHER INFORMATION: Synthetic

<400> SEQUENCE: 15
ctcccgacgt cgctacg                                                  17

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
cgccgaggcg gttttttgcg                                               20

<210> SEQ ID NO 17
<211> LENGTH: 18
<212> TYPE: DNA
<213> ORGANISM: Artificial Sequence
<220> FEATURE:
<223> OTHER INFORMATION: Synthetic

<400> SEQUENCE: 17
tcgttgggta aggcgttc                                                 18

<210> SEQ ID NO 18
<211> LENGTH: 18
<212> TYPE: DNA
<213> ORGANISM: Artificial Sequence
<220> FEATURE:
<223> OTHER INFORMATION: Synthetic

<400> SEQUENCE: 18
```

```
aaacgaacac ccgaaccg                                                  18

<210> SEQ ID NO 19
<211> LENGTH: 22
<212> TYPE: DNA
<213> ORGANISM: Artificial Sequence
<220> FEATURE:
<223> OTHER INFORMATION: Synthetic

<400> SEQUENCE: 19
gacgcggagg cggttttttg tt                                             22

<210> SEQ ID NO 20
<211> LENGTH: 15
<212> TYPE: DNA
<213> ORGANISM: Artificial Sequence
<220> FEATURE:
<223> OTHER INFORMATION: Synthetic

<400> SEQUENCE: 20
gcgggaggag gtgcc                                                     15

<210> SEQ ID NO 21
<211> LENGTH: 27
<212> TYPE: DNA
<213> ORGANISM: Artificial Sequence
<220> FEATURE:
<223> OTHER INFORMATION: Synthetic

<400> SEQUENCE: 21
tttgtttttt tgattaggtg tttaaga                                        27

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
caccaacctc ataaccttat c                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23
ccacggacga tagtgttgtg g                                              21

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
aggcctgctg aaaatgactg                                                20

<210> SEQ ID NO 25
<211> LENGTH: 22
<212> TYPE: DNA
```

```
<213> ORGANISM: Artificial Sequence
<220> FEATURE:
<223> OTHER INFORMATION: Synthetic

<400> SEQUENCE: 25
ctattgttgg atcatattcg tc                                           22

<210> SEQ ID NO 26
<211> LENGTH: 19
<212> TYPE: DNA
<213> ORGANISM: Artificial Sequence
<220> FEATURE:
<223> OTHER INFORMATION: Synthetic

<400> SEQUENCE: 26
cttgtggtag ttggagcaa                                               19

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
gcgcgtccag tggcgtaggc                                              20

<210> SEQ ID NO 28
<211> LENGTH: 22
<212> TYPE: DNA
<213> ORGANISM: Artificial Sequence
<220> FEATURE:
<223> OTHER INFORMATION: Synthetic

<400> SEQUENCE: 28
aaacttgtgg tagttggacc tt                                           22

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
gcgcgtcctg tggcgtaggc                                              20

<210> SEQ ID NO 30
<211> LENGTH: 24
<212> TYPE: DNA
<213> ORGANISM: Artificial Sequence
<220> FEATURE:
<223> OTHER INFORMATION: Synthetic

<400> SEQUENCE: 30
tataaacttg tggtagttgg acct                                         24

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
gcgcgtcccg tggcgtaggc                                              20
```

<210> SEQ ID NO 32
<211> LENGTH: 21
<212> TYPE: DNA
<213> ORGANISM: Artificial Sequence
<220> FEATURE:
<223> OTHER INFORMATION: Synthetic

<400> SEQUENCE: 32
acttgtggta gttggagctc a                                             21

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
gcgcgtccat ggcgtaggca                                               20

<210> SEQ ID NO 34
<211> LENGTH: 21
<212> TYPE: DNA
<213> ORGANISM: Artificial Sequence
<220> FEATURE:
<223> OTHER INFORMATION: Synthetic

<400> SEQUENCE: 34
acttgtggta gttggagctc t                                             21

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
gcgcgtcctt ggcgtaggca                                               20

<210> SEQ ID NO 36
<211> LENGTH: 22
<212> TYPE: DNA
<213> ORGANISM: Artificial Sequence
<220> FEATURE:
<223> OTHER INFORMATION: Synthetic

<400> SEQUENCE: 36
aacttgtggt agttggagat gc                                            22

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
gcgcgtccct ggcgtaggca                                               20

<210> SEQ ID NO 38
<211> LENGTH: 18
<212> TYPE: DNA
<213> ORGANISM: Artificial Sequence
<220> FEATURE:

```
<223> OTHER INFORMATION: Synthetic

<400> SEQUENCE: 38
ggtagttgga gctggtca                                              18

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
gcgcgtccac gtaggcaaga                                            20

<210> SEQ ID NO 40
<211> LENGTH: 22
<212> TYPE: DNA
<213> ORGANISM: Artificial Sequence
<220> FEATURE:
<223> OTHER INFORMATION: Synthetic

<400> SEQUENCE: 40
ctattgttgg atcatattcg tc                                         22
```